United States Patent
Saya et al.

(10) Patent No.: US 11,814,651 B2
(45) Date of Patent: Nov. 14, 2023

(54) CELL AND UTILIZATION THEREOF

(71) Applicant: FUJITA ACADEMY, Aichi (JP)

(72) Inventors: Hideyuki Saya, Tokyo (JP); Yoshimi Arima, Tokyo (JP); Takashi Semba, Tokyo (JP); Akiyoshi Kasuga, Tokyo (JP)

(73) Assignee: FUJITA ACADEMY, Aichi (JP)

( * ) Notice: Subject to any disclaimer, the term of this patent is extended or adjusted under 35 U.S.C. 154(b) by 778 days.

(21) Appl. No.: 16/490,786

(22) PCT Filed: Mar. 7, 2018

(86) PCT No.: PCT/JP2018/008735
§ 371 (c)(1),
(2) Date: Sep. 3, 2019

(87) PCT Pub. No.: WO2018/164174
PCT Pub. Date: Sep. 13, 2018

(65) Prior Publication Data
US 2020/0017834 A1    Jan. 16, 2020

(30) Foreign Application Priority Data
Mar. 7, 2017    (JP) ................... 2017-042659

(51) Int. Cl.
| | |
|---|---|
| *C12N 5/071* | (2010.01) |
| *A01K 67/027* | (2006.01) |
| *A61K 49/00* | (2006.01) |
| *C12N 5/095* | (2010.01) |
| *C12Q 1/02* | (2006.01) |

(52) U.S. Cl.
CPC .......... *C12N 5/0689* (2013.01); *A01K 67/027* (2013.01); *A61K 49/0008* (2013.01); *C12N 5/0695* (2013.01); *C12Q 1/025* (2013.01); *A01K 2207/12* (2013.01); *A01K 2227/105* (2013.01); *A01K 2267/0331* (2013.01); *C12N 2500/30* (2013.01); *C12N 2500/90* (2013.01); *C12N 2501/11* (2013.01); *C12N 2501/117* (2013.01); *C12N 2506/27* (2013.01); *C12N 2513/00* (2013.01)

(58) Field of Classification Search
CPC . C12N 5/0689; C12N 5/0695; C12N 2506/27
See application file for complete search history.

(56) References Cited

U.S. PATENT DOCUMENTS

2011/0206735 A1    8/2011    Qian

FOREIGN PATENT DOCUMENTS

WO    WO 2007/149447 A2    12/2007

OTHER PUBLICATIONS

Teisanu (Am J Respir Cell Mol Biol vol. 44. pp 794-803, 2011).*
Su (The EMBO Journal (2009) 28, 1904-1915).*
Japanese Office Action for JP Application No. 2019-504632, dated Mar. 1, 2022, 8 pages.
Borena et al., "Mammary Stem Cell Research in Veterinary Science: An Update", Stem Cells and Development, Jun. 15, 2013, vol. 22, No. 12, pp. 1743-1751, XP055740396.
Supplementary European Search Report for European Patent Application No. 18764903.3, dated Oct. 26, 2020, 10 pages.
Collisson E. A., et al., Comprehensive molecular profiling of lung adenocarcinoma, Nature 511 (7511), 543-550, 2014.
Semba et al., Cancer Research, Abstract 4255: EpCAM positive lung cells are involved in organoid formation, Jul. 2016.
Kai et al., Oncogene, Jan. 23, 2014:33(4) 440-448.
Shimizu et al., Oncogene (2010) 29, 5687-5699.
Fisher et al., Genes & Development 15:3249-3262, 2001.
Aguirre et al., Genes & Development 17:3112-3126, 2003.
International Search Report in PCT Application No. PCT/JP2018/008735, dated May 29, 2018 (4 pages).
Arima et al., "Generation of mouse lung cancer model by introducing KRASG12V, EML4-ALK, EZR-ROS1 or KIF5B-RET genes into Ink4a/Arf knockout mouse lung cells", The 74th Annual Meeting of the Japanese Cancer Association, Oct. 8, 2015, P-1042.
International Search Report for International Application No. PCT/JP2018/008735, dated May 29, 2018 (4 pages).
Onishi et al., The 36th Annual Meeting of the Molecular Biology Society of Japan, 3P-0865, Construction and analysis of ALK carcinogenesis model using neural stem cell, 2013.

* cited by examiner

Primary Examiner — Valarie E Bertoglio
(74) Attorney, Agent, or Firm — LATHROP GPM LLP; Brian C. Trinque

(57) ABSTRACT

Provided is an epithelial tissue stem cell derived from an adult, which lacks at least one tumor suppressor gene.

8 Claims, 14 Drawing Sheets

CELL AND UTILIZATION THEREOF

TECHNICAL FIELD

The present invention relates to a cell and utilization thereof. More specifically, the present invention relates to an epithelial tissue stem cell derived from an adult, a method for producing a cell culture, a cell culture, an organoid, a method for screening a cell transforming agent, a method for screening an anticancer agent, a method for producing a cancer-bearing non-human animal model, a cancer-bearing non-human animal model, a method for evaluating a test substance, a method for producing a cancer stem cell, a cancer stem cell, and a method for screening an anticancer agent effective for a cancer stem cell.

Priority is claimed on Japanese Patent Application No. 2017-042659, filed Mar. 7, 2017, the content of which is incorporated herein by reference.

BACKGROUND ART

For example, lung cancer is one of typical intractable cancers. In recent years, various gene mutations associated with lung cancer have been found by large-scale genetic analysis of lung cancer using human samples (refer to, for example, Non Patent Literature 1).

It has become clear that detecting a specific gene mutation and selecting an appropriate therapeutic drug are effective in a case of using molecularly targeted drugs for the treatment of lung cancer. However, the association between various gene mutations and the effects of therapeutic agents for cancer that have been found in recent years has not been sufficiently elucidated. In order to clarify the effects of therapeutic agents for cancer having a specific gene mutation, it is necessary to produce a cancer-bearing animal model having the gene mutation and evaluate the effects of therapeutic agents.

CITATION LIST

Non-Patent Literature

[Non-Patent Literature 1] Collisson E. A., et al., Comprehensive molecular profiling of lung adenocarcinoma, Nature 511 (7511), 543-550, 2014.

DISCLOSURE OF INVENTION

Technical Problem

Currently, xenograft mouse models, genetically modified mouse models, allograft mouse models, and the like are known as cancer-bearing animal models.

A xenograft mouse model is a model in which cancer cells derived from a human are transplanted into immunodeficient mice. Because the animal species of cancer cells and cells surrounding the cancer are different in xenograft mouse models, their interaction cannot be completely reproduced. In addition, since a host is an immunodeficient mouse, it is difficult to evaluate a phenomenon involving the immune system.

Regarding genetically modified mouse models, a long period of time is required for production. In addition, it is difficult to produce a tumor model formed from a plurality of cells each having a plurality of different mutations. For this reason, it is difficult to produce various cancer-bearing animal models corresponding to the various gene mutations found in recent years.

On the other hand, an allograft mouse model is a model in which cancer cells derived from a mouse are transplanted into a syngeneic mouse having a normal immune system. An allograft mouse model can be conveniently produced, and interaction between tumors and immune cells can also be studied. However, there are very few cancer cell lines derived from a mouse, and there are no methods for producing various model cells which are cells present in a living body, and which correspond to the various gene mutations found in recent years. Therefore, it has been difficult to produce a cell model having various gene mutations, and non-human animal models.

With such background, an object of the present invention is to provide a technique for easily producing a cancer-bearing animal model that has cancer cells having various gene mutations and has a normal immune system.

Solution to Problem

The present invention includes the following aspects.

[1] An epithelial tissue stem cell derived from an adult, which lacks at least one tumor suppressor gene.

[2] The cell according to [1], which is an Epithelial cell adhesion molecule (EpCAM)$^+$CD31$^-$CD45$^-$.

[3] The cell according to [1] or [2], which expresses EpCAM and Stem cell antigen-1 (Sca-1), or expresses Surfactant protein-C (SPC) and Secretoglobin family 1A member 1 (CC10).

[4] The cell according to any one of [1] to [3], which expresses Lymphocyte antigen 6 family member D (Ly6D).

[5] The cell according to [1] or [2], which expresses Cytokeratin 19 (CK19).

[6] The cell according to any one of [1] to [5], in which the tumor suppressor gene is selected from the group consisting of Ink4a/Arf, p53, and PTEN.

[7] The cell according to any one of [1] to [6], which further expresses at least one oncogene.

[8] The cell according to [7], in which the oncogene is a mutated KRAS gene, a mutated EGFR gene, an ALK fusion gene, or a ROS1 fusion gene.

[9] A method for producing a cell culture containing 50% or more of epithelial tissue stem cells derived from an adult, the method including a step of three-dimensionally (3D) culturing the cell according to any one of [1] to [8].

[10] A cell culture produced by the method according to [9].

[11] An organoid including the cell according to any one of [1] to [8] or a cell derived from the cell culture according to [10].

[12] A method for screening a cell transforming agent, including: a step of culturing the cell according to any one of [1] to [6] in the presence of a test substance; and a step of evaluating characteristics of the cells.

[13] A method for screening an anticancer agent, including: a step of culturing the cell according to any one of [6] to [8], a cell derived from the cell culture according to [10], or the organoid according to [11] in the presence of a test substance; and a step of measuring proliferation of the cell or the organoid.

[14] A method for producing a cancer-bearing non-human animal model, including a step of transplanting the cell according to [7] or [8], a cell derived from the cell culture according to [10], or the organoid according to [11] into a non-human animal.

[15] The method for producing according to [14], in which the non-human animal is a non-human animal having a normal immune system.

[16] A cancer-bearing non-human animal model, which is produced by the method for producing according to [14] or [15].

[17] A method for evaluating a test substance, including: a step of administering a test substance to the cancer-bearing non-human animal model according to [16]; and a step of evaluating a prognosis of the cancer-bearing non-human animal model.

[18] The evaluation method according to [17], in which the test substance is a combination of an anticancer agent and an immune agonist.

[19] A method for producing a cancer stem cell, including a step of 3D culturing a cell derived from a tumor formed at a transplantation site of the cancer-bearing non-human animal model according to [16].

[20] A cancer stem cell which is established from a tumor formed at a transplantation site of the cancer-bearing non-human animal model according to [16].

[21] A method for producing a cancer stem cell, including a step of 3D culturing a cell derived from a tumor newly formed at a site other than a transplantation site of the cancer-bearing non-human animal model according to [16].

[22] A cancer stem cell which is established from a tumor newly formed at a site other than a transplantation site of the cancer-bearing non-human animal model according to [16].

[23] A method for screening an anticancer agent effective for cancer stem cells, including: a step of culturing the cancer stem cell according to [20] or [22] in the presence of a test substance; and a step of measuring proliferation of the cancer stem cell.

The present invention can be said to include the following aspects.

[P1] A bronchioalveolar stem cell, which lacks at least one tumor suppressor gene.

[P2] The cell according to [P1], which expresses Epithelial cell adhesion molecule (EpCAM) and Stem cell antigen-1 (Sca-1), or expresses Surfactant protein-C (SPC) and Secretoglobin family 1A member 1 (CC10).

[P3] The cell according to [P1] or [P2], in which the tumor suppressor gene is selected from the group consisting of Ink4a/Arf, p53, and PTEN.

[P4] The cell according to any one of [P1] to [P3], which further expresses at least one oncogene.

[P5] The cell according to [P4], in which the oncogene is a mutated KRAS gene, a mutated EGFR gene, an ALK fusion gene, or a ROS1 fusion gene.

[P6] An organoid including the cell according to any one of [P1] to [P5].

[P7] A method for screening an anticancer agent, including: a step of culturing the cell according to [P4] or [P5], or the organoid according to [P6] in the presence of a test substance; and a step of measuring proliferation of the cell or the organoid.

[P8] A method for producing a cancer-bearing non-human animal model, including a step of transplanting the cell according to [P4] or [P5], or the organoid according to [P6] into a non-human animal.

[P9] The production method according to [P8], in which the non-human animal is a non-human animal having a normal immune system.

[P10] A cancer-bearing non-human animal model, which is produced by the production method according to [P8] or [P9].

[P11] A method for evaluating a test substance, including: a step of administering a test substance to the cancer-bearing non-human animal model according to [P10]; and a step of evaluating a prognosis of the cancer-bearing non-human animal model.

[P12] The evaluation method according to [P11], in which the test substance is a combination of an anticancer agent and an immune agonist.

Advantageous Effects of Invention

According to the present invention, it is possible to provide a technique for easily producing a cancer-bearing animal model that has cancer cells having various gene mutations and has a normal immune system.

BRIEF DESCRIPTION OF DRAWINGS

FIGS. 7(a) and 7(c) are micrographs in bright field, and FIGS. 7(b) and 7(d) are fluorescence micrographs.

BEST MODE FOR CARRYING OUT THE INVENTION

[Cell]

Figure 1:
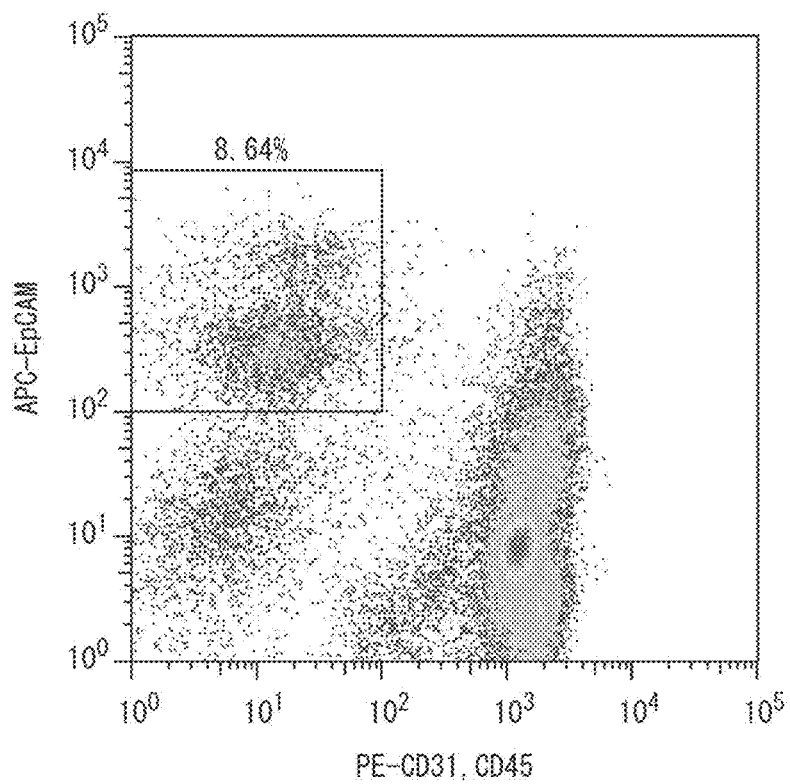
FIG. 1 shows data of flow cytometry in a case where $CD31^-CD45^-EpCAM^+$ lung cells were sorted in Experimental Example 2.

In one embodiment, the present invention provides a cultured epithelial cell, which lacks at least one tumor suppressor gene. The cultured epithelial cell of the present embodiment may be an epithelial tissue stem cell derived from an adult.

The cell of the present embodiment is not particularly limited as long as it is derived from the epithelium of animal tissue, and may be, for example, a Bronchioalveolar stem cell (BASC), may be, for example, a bile duct epithelial cell, or may be, for example, a gallbladder epithelial cell. In addition, the cell of the present embodiment may be an epithelial cell other than a gastrointestinal epithelial cell.

As will be described later in Examples, the inventors of the present invention have clarified that it is possible to easily produce a cancer-bearing non-human animal model by introducing an arbitrary oncogene into the cell of the present embodiment and transplanting the cell into an allogeneic non-human animal having a normal immune system. Accordingly, the cell of the present embodiment is useful as a host cell into which an arbitrary oncogene is to be introduced.

The cell of the present embodiment may be a cell derived from a human or a cell derived from a non-human animal. Examples of non-human animals include cats, dogs, horses, monkeys, cows, sheep, pigs, goats, rabbits, hamsters, guinea pigs, rats, mice, and the like. In addition, the cell of the present embodiment is preferably a cell derived from a lung.

The cell of the present embodiment is preferably EpCAM$^+$ CD31$^-$CD45$^-$. As will be described later in Examples, the cell of the present embodiment can be obtained by recovering EpCAM$^+$CD31$^-$CD45$^-$ from tissues such as lung, gallbladder, and biliary duct and 3D culturing it.

The cell of the present embodiment may express EpCAM and Sca-1, or may express SPC and CC10. As will be described later in Examples, the cell of the present embodiment may be a bronchioalveolar stem cell in which sternness is maintained at high levels. Co-expression of EpCAM with Sca-1 or co-expression of SPC with CC10 is a marker for BASC. That is, an EpCAM$^+$Sca-1$^+$ cell or an SPC$^+$CC10$^+$ cell is BASC.

The cell of the present embodiment may be an EpCAM$^+$ Sca-1$^+$SPC$^+$ cell, may be an EpCAM$^+$ Sca-1$^+$CC10$^+$ cell, may be an EpCAM$^+$SPC$^+$CC10$^+$ cell, may be a Sca-1$^+$SPC$^+$CC10$^+$ cell, or may be an EpCAM$^+$Sca-1$^+$SPC$^+$CC10$^+$ cell.

In addition, a RefSeq ID of a human EpCAM protein is NP_002345.2, and a RefSeq ID of a mouse EpCAM protein is NP_032558.2. In addition, a RefSeq ID of a mouse Sca-1 protein is NP_001258345.1. In a case where cells of animal species other than those described above are used, cells expressing homologs thereof may be used.

In addition, a RefSeq ID of a human SPC protein is NP_001165828.1, NP_001304707.1, NP_001304708.1, and the like, and a RefSeq ID of a mouse SPC protein is NP_035489.2. In addition, a RefSeq ID of a human CC10 protein is NP_003348.1, and a RefSeq ID of a mouse CC10 protein is NP_035811.1. In a case where cells of animal species other than those described above are used, cells expressing homologs thereof may be used.

In addition, as will be described later in Examples, the cell of the present embodiment may express Ly6D. Furthermore, as will be described later in Examples, the cell of the present embodiment may express CK19.

A RefSeq ID of a human Ly6D protein is NP_003686.1 and the like, and a RefSeq ID of a mouse Ly6D protein is NP_034872.1 and the like. In addition, a RefSeq ID of a human CK19 protein is NP_002267.2 and the like, and a RefSeq ID of a mouse CK19 protein is NP_032497.1 and the like. In a case where cells of animal species other than those described above are used, cells expressing homologs thereof may be used.

In the cell of the present embodiment, examples of tumor suppressor genes include Ink4a/Arf, p53, PTEN, and the like.

The cell of the present embodiment may be prepared from a non-human animal in which the above-mentioned tumor suppressor gene is disrupted. Alternatively, at least one tumor suppressor gene may be deleted by separating cells expressing EpCAM and Sca-1, EpCAM$^+$CD31$^-$CD45$^-$ cells, that is, cells expressing EpCAM and not expressing CD31 and CD45, cells expressing Ly6D, cells expressing CK19, and the like by flow cytometry, a method using antibody-modified magnetic beads and a magnetic stand, and the like, and then editing a genome, and introducing a shRNA expression vector, and the like. In the present specification, deleting a gene means to lower or delete a function of a target gene by deleting at least a part of the target gene, lowering expression of the target gene, and the like.

As will be described later in Examples, by 3D culturing the cell of the present embodiment in a serum-free medium, it can be maintained in a state containing abundant bronchioalveolar stem cells (BASCs), bile duct epithelial cells, and gallbladder epithelial cells, in a state where the stem cell property is maintained high, and thereby various forms of organoid can be formed. A method for 3D culturing is not particularly limited, and examples thereof include a method using Matrigel, a method using collagen, a method using laminin, and the like.

Accordingly, in one embodiment, the present invention can also be said to provide a method for producing a cell culture containing 50% or more of epithelial stem cells, the method including a step of 3D culturing the cell of the above-described embodiment. The present invention also provides a cell culture containing 50% or more of epithelial stem cells. The epithelial stem cells may be epithelial tissue stem cells derived from an adult.

The cell of the present embodiment may further express at least one oncogene. As will be described later in Examples, a tumor can be formed by transplanting, into an animal, the cell of the present embodiment into which an oncogene has been introduced.

The oncogene to be introduced into the cell of the present embodiment is not particularly limited, and cancer-related genes having various gene mutations found in recent years can be used. More specific examples thereof include a mutated KRAS gene, a mutated EGFR gene, an ALK fusion gene, a ROS1 fusion gene, and the like.

Examples of mutated KRAS genes include $KRAS^{G12V}$, $KRAS^{G12D}$, and the like. Examples of ALK fusion genes include EML4-ALK, KIF5B-ALK, and the like.

As will be described later in Examples, the cell of the present embodiment into which an oncogene has been introduced can be maintained by 3D culturing in a serum-free medium.

Accordingly, in one embodiment, the present invention can also be said to provide a method for producing a cell culture containing 50% or more of epithelial stem cells, the method including a step of 3D culturing the cell of the above-described embodiment into which an oncogene has been introduced. The present invention also provides a cell culture containing 50% or more of epithelial stem cells. The epithelial stem cells may be epithelial tissue stem cells derived from an adult.

In addition, the cell of the present embodiment into which an oncogene has been introduced can also form various forms of organoid. Accordingly, the cell of the present embodiment may be an organoid. In the present specification, the term "organoid" means an organ-like tissue obtained by 3D culturing cells. Furthermore, in the present specification, a cell mass obtained by culturing the cell of the present embodiment is also included in this organoid.

[Method for Screening Cell Transforming Agent]

In one embodiment, the present invention provides a method for screening a cell transforming agent, the method including a step of culturing the above-described cell, a cell derived from the above-described cell culture, or the above-described organoid in the presence of a test substance; and a step of evaluating characteristics of the cells. In the screening method of the present embodiment, the cell or organoid may be a cell or organoid which lacks at least one tumor suppressor gene and into which no oncogene has been introduced.

Cell characteristics to be evaluated in the screening method of the present embodiment include differentiation and dedifferentiation. Cell differentiation and dedifferentiation can be evaluated by, for example, microscopic observation, measurement of expression of a marker gene or a marker protein, and the like.

In addition, examples of cell transforming agents include differentiation-inducing agents, dedifferentiation-inducing agents, differentiation inhibitors, dedifferentiation-inducing agents, and the like.

[Method for Screening Anticancer Agent]

In one embodiment, the present invention provides a method for screening an anticancer agent, the method including a step of culturing the above-described cell, a cell derived from the above-described cell culture, or the organoid in the presence of a test substance; and a step of measuring proliferation of the cell or the organoid. The above-described cell or organoid is a cultured epithelial cell or organoid obtained by culturing this cell, which lacks at least one tumor suppressor gene, and expresses at least one oncogene or does not express an oncogene. As described above, examples of cultured epithelial cells include bronchioalveolar stem cells, bile duct epithelial cells, gallbladder epithelial cells, and the like.

The anticancer agent screened by the method of the present embodiment can also be said to be an anticancer agent effective for cancer stem cells.

In the screening method of the present embodiment, an oncogene is not particularly limited, and examples thereof include the same as those described above.

The test substance is not particularly limited, and examples thereof include compound libraries such as natural compound libraries and synthetic compound libraries, existing drug libraries, metabolite libraries, and the like. Specifically, the test substance may be added to a medium of the cells described above to examine the influence on cell proliferation. More specifically, for example, cells are seeded in a well plate and cultured in the presence of a compound library for about 1 to 30 days. The culture may be performed by, for example, by 3D culture using a serum-free medium, or by general culture using a medium containing serum.

Thereafter, proliferation of the cell or organoid is measured by measuring the number of viable cells by, for example, color development due to reduction of tetrazolium salts. Compounds that inhibit the proliferation of the cell or organoid are candidates for the anticancer agent. As a tetrazolium salt, commercially available 3-[4,5-dimethylthiazol-2-yl]-2,5-diphenyltetrazolium bromide (MTT) or the like can be used.

According to the screening method of the present embodiment, it is possible to rapidly screen an anticancer agent that can effectively treat cancers having various gene mutations found in recent years.

[Cancer-Bearing Non-Human Animal Model]

In one embodiment, the present invention provides a cancer-bearing non-human animal model into which the cultured epithelial cell or organoid obtained by culturing this cell, which lacks at least one tumor suppressor gene, and expresses at least one oncogene, has been transplanted. The present invention further provides a method for producing a cancer-bearing non-human animal model, including a step of transplanting the cultured epithelial cell or organoid obtained by culturing this cell, which lacks at least one tumor suppressor gene, and expresses at least one oncogene. As described above, examples of cultured epithelial cells include bronchioalveolar stem cells, bile duct epithelial cells, gallbladder epithelial cells, and the like.

Regarding allograft mouse models of the related art, because there are very few cancer cell lines derived from a mouse, it has been difficult to produce various models corresponding to various gene mutations.

On the other hand, according to the cancer-bearing non-human animal model of the present embodiment, it is possible to produce various cancer-bearing non-human animal model rapidly and easily using cells into which an arbitrary oncogene has been introduced. Accordingly, by analyzing the cancer-bearing non-human animal model of the present embodiment, it is possible to clarify the characteristics of cancers having various gene mutations found in recent years, and to develop a therapeutic method therefor.

In transplantation of cells into non-human animals, the above-described organoid may be transplanted, or cells forming the organoid may be transplanted after being dispersed into a single cell.

In addition, a transplantation site is not particularly limited, and examples include subcutaneous tissues, the subcapsular kidney, lung, tail vein, abdominal cavity, heart cavity, liver, and the like.

In addition, examples of non-human animals include cats, dogs, horses, monkeys, cows, sheep, pigs, goats, rabbits, hamsters, guinea pigs, rats, mice, and the like.

The cancer-bearing non-human animal model of the present embodiment may be an immunodeficient non-human animal or a non-human animal having a normal immune system. In a case where a non-human animal having a normal immune system is used, the interaction with cancer cells, immune cells, and tissues around a tumor can be analyzed. In recent years, in addition to therapeutic agents targeting cancer cells, therapeutic agents targeting tumor vessels, tumor immunity, and the like have been developed, which is diversification of therapeutic agents for cancer. Accordingly, the cancer-bearing non-human animal model of the present embodiment is also useful for development and evaluation of such a therapeutic agent.

As will be shown in Examples, according to the cancer-bearing non-human animal model of the present embodiment, it is possible to form glandular structures that pathologically reflect human lung cancer tissues. Accordingly, it can be suitably used, for example, to develop a method for treating lung cancer.

[Method for Evaluating Test Substance]

In one embodiment, the present invention provides a method for evaluating a test substance, the method including: a step of administering a test substance to the above-described cancer-bearing non-human animal model; and a step of evaluating a prognosis of the cancer-bearing non-human animal model.

As described above, as the cancer-bearing non-human animal model, non-human animals having a normal immune system can be used. Accordingly, according to the evaluation method of the present embodiment, the interaction between cancer cells having various gene mutations and immune cells can be evaluated.

As described above, in the cancer-bearing animal models of the related art, it has been difficult to evaluate an effect of a combination of, for example, an anticancer agent and an immune agonist because of a host being immunodeficient or difficulty in production of the model. On the other hand, according to the evaluation method of the present embodiment, a combination of an anticancer agent and an immune agonist can also be used as a test substance.

The anticancer agent is not particularly limited, and an existing drug or a drug to be developed in the future can be used. Specific examples thereof include antimetabolic drugs such as gemcitabine and pemetrexed; molecularly targeted drugs such as gefitinib, erlotinib, crizotinib, and alectinib; and the like.

In addition, the immune agonist is not particularly limited, and an existing drug or a drug to be developed in the future can be used. Specific examples thereof include TLR agonists such as imiquimod and resiquimod; immune checkpoint inhibitors such as nivolumab, ipilimumab, and penbrolizumab; and the like.

Administration of the test substance may be performed orally, or may be performed by intravenous injection, intraperitoneal injection, inhalation, application to the skin, and the like.

In the evaluation method of the present embodiment, evaluation of a prognosis is not particularly limited. For example, a size of tumor tissue, evaluation of cancer metastasis, a change in body weight, a survival rate, fluorescence imaging images, luminescence imaging images, and the like may be evaluated.

The test substance can be judged to be effective as a therapeutic agent for cancer in a case where a prognosis for the cancer-bearing non-human animal model is favorable when the test substance is administered, as compared to a case in which a control substance is administered. Accordingly, the evaluation method of the present embodiment can be said to be a method for screening a therapeutic agent for cancer.

[Method for Producing Cancer Stem Cell and Cancer Stem Cell]

In one embodiment, the present invention provides a method for producing a cancer stem cell, the method including a step of 3D culturing a cell derived from a tumor formed at a transplantation site of the above-described cell or organoid in the above-described non-human animal cancer-bearing model.

According to the production method of the present embodiment, it is possible to produce a cell population containing a high proportion of cancer cells in a state in which sternness is maintained at high levels, that is, cancer stem cells. The production method of the present embodiment can be said to be a method for concentrating a cancer stem cell.

A method for 3D culturing is not particularly limited, and examples thereof include a method using Matrigel, a method using collagen, a method using laminin, and the like.

In one embodiment, the present invention provides a cancer stem cell established by the above production method. The cancer stem cell of the present embodiment is a cancer stem cell which lacks at least one tumor suppressor gene and express various oncogenes. Accordingly, it is considered that there are differences in naturally occurring cancer stem cells in combinations of expressed marker proteins, epigenetic changes, and the like. However, it is difficult to identify such combinations of marker proteins and epigenetic changes.

In one embodiment, the present invention provides a method for producing a cancer stem cell, the method including a step of 3D culturing a cell derived from a tumor newly formed at a site other than a transplantation site of the above-described cell or organoid in the above-described non-human animal cancer-bearing model.

According to the production method of the present embodiment, cancer stem cells derived from a tumor that has metastasized from a primary lesion can be produced. A method for 3D culturing is not particularly limited, and examples thereof include a method using Matrigel, a method using collagen, a method using laminin, and the like.

In one embodiment, the present invention provides a cancer stem cell established by the above production method. The cancer stem cell of the present embodiment is a cancer stem cell which lacks at least one tumor suppressor gene and expresses various oncogenes, and is a cancer stem cell having a history of metastasis from a primary lesion. Accordingly, it is considered that there are differences in naturally occurring cancer stem cells in combinations of expressed marker proteins, epigenetic changes, and the like. However, it is difficult to identify such combinations of marker proteins and epigenetic changes.

[Method for Screening for Anticancer Agent Effective for Cancer Stem Cell]

In one embodiment, the present invention provides a method for screening an anticancer agent effective for a cancer stem cell, the method including: a step of culturing the above-described cancer stem cell in the presence of a test substance; and a step of measuring proliferation of the cancer stem cell.

The cancer stem cell in the screening method of the present embodiment is a cancer stem cell derived from a tumor formed at a transplantation site of the above-described cell or organoid, or a tumor newly formed at a site other than the transplantation site in the above-described non-human animal cancer-bearing model.

In the screening method of the present embodiment, the test substance is the same as that described above, and examples thereof include compound libraries, existing drug libraries, metabolite libraries, and the like. In addition, measurement of cell proliferation can be performed in the same manner as described above, and measurement can be performed by, for example, color development due to reduction of tetrazolium salts.

EXAMPLES

Next, the present invention will be described in more detail by showing experimental examples, but the present invention is not limited to the following experimental examples.

Experimental Example 1

(Separation of Ink4a/Arf$^{-/-}$ Mice Lung Cell)

Lung cells were isolated from Ink4a/Arf$^{-/-}$ mice (obtained from Mouse Models of Human Cancers Consortium (NCI-Frederick)). Specifically, first, 0.3 mL of pentobarbital (a final concentration of 7.2 mg/mL, Kyoritsu Seiyaku, cat. no. SOM02-YA1312) per mouse was intraperitoneally injected to the Ink4a/Arf$^{-/-}$ C57BL6/J mice for anesthetization.

Subsequently, the mouse was fixed in a supine position, the skin was incised in midline from the lower abdomen to the chin, and the skin was exfoliated to right and left sides. Subsequently, the submandibular gland was removed, and the peritracheal muscle groups were incised to expose the trachea. Subsequently, the peritoneal membrane was incised in a T-shape along the median and calcaneal arch to expose the abdominal aorta and the inferior vena cava. Subsequently, the left and right carotid arteries, the abdominal aorta, and the inferior vena cava were cut off, and phlebotomization was sufficiently performed.

Subsequently, the diaphragm and thorax were then removed to expose the lungs and heart, the left ventricle was cleaved, 15 mL of a phosphate buffer (PBS) cooled in advance was injected from the right ventricle using a syringe and a 23-gauge needle, and blood in the lungs was washed out.

Subsequently, a 22-gauge vein indwelling needle was inserted into the trachea, and 1.5 ml of collagenase/dispase (a final concentration of 2.5 mg/mL, Roche, cat. no. 11097113001) was injected into the lung using a syringe. Thereafter, the syringe was quickly replaced, and 0.5 mL of agarose (a final concentration of 0.5%, Nacalai Tesque, cat. no. 02468-95) was injected.

Subsequently, ice was placed on the lungs to harden the agarose. After 2 minutes, the ice removed, and each lung lobe was extracted and transferred to a conical tube containing collagenase/dispase, and the tube was left to stand in a 37° C. thermostat for 10 minutes.

Subsequently, enzyme-treated lung tissue was minced with scissors, and then transferred to a conical tube containing collagenase/dispase again. The tube was shaken at 37° C. for 45 minutes. Subsequently, DNase I (a final concentration of 0.5 mg/mL, Sigma, cat. no. DN25-1G) was added to the solution. Pipetting was performed 50 to 60 times with a 1000 μL pipette, and the cells were allowed to pass through a 100 μm cell strainer (Falcon, cat. no. 352360). Subsequently, the mixture was centrifuged at 200×g at 4° C. for 3 minutes. After removing the supernatant, 10 mL of erythrocyte hemolysis buffer was added, and the cells were allowed to pass through a 40 μm cell strainer (Falcon, cat. no. 352340). Subsequently, the cells were centrifuged at 200×g at 4° C. for 3 minutes. After removing the supernatant, the cells were suspended in 10% fetal bovine serum (FBS)/PBS (a washing buffer), and thereby lung cells were obtained.

Experimental Example 2

(Separation of CD31$^-$CD45$^-$EpCAM$^+$ Lung Cell)

From the lung cells prepared in Experimental Example 1, CD31$^-$CD45$^-$EpCAM$^+$ lung cells were sorted and separated using a flow cytometer (type "MoFlo XDP flow cytometer," Beckman Coulter, Inc.). In addition, CD31 is a marker of vascular endothelial cells, CD45 is a pancytopenia marker, and EpCAM is a marker of lung epithelial cells.

The following were used as antibodies and coloring agents: Phycoerythrin (PE)-labeled anti-mouse CD31 rat monoclonal antibody (Biolegend, cat. no. 102408), PE-labeled anti-mouse CD45 rat monoclonal antibody (eBioscience, cat. no. 12-0451-83), PE-labeled rat immunoglobulin G2b (IgG2b) isotype control (eBioscience, cat. no. 12-4031-83), Allophycocyanin (APC)-labeled anti-mouse CD326 (EpCAM) rat monoclonal antibody (Bio Legend, cat. no. 118241), APC-labeled rat IgG2aκ isotype control (Bio Legend, cat. no. 400512), and Propidium iodide (PI) (Sigma, no. P4170-10MG).

FIG. 1 shows data of flow cytometry in a case where CD31$^-$CD45$^-$EpCAM$^+$ lung cells were sorted. The cells in the boxed area in the drawing were recovered.

Experimental Example 3

(Culture of CD31$^-$CD45$^-$EpCAM$^+$ Lung Cell)

50 μL of Matrigel (Corning, cat. no. 356230) was put into a 0.4 μm cell culture insert (Falcon, cat. no. 353095) in advance, and allowed to stand at 37° C. for 30 minutes for gelation.

As a base medium, DMEM/Ham's F-12 with L-glutamine (Wako, cat. no. 048-29785), 1×B-27 supplement (Gibco, cat. no. 12587-010), HEPES (a final concentration of 15 mM, Gibco, no. 15630-080), Epidermal growth factor (a final concentration of 20 ng/mL, Peprotech, cat. no. AF-100-15), Keratinocyte growth factor (a final concentration of 10 ng/mL, Biolegend, cat. no. 752240), and ROCK inhibitor (service preparation, a final concentration of 10 μM, Merck Millipore, cat. no. 688000-1MG), which are serum-free media, were used.

After counting the number of cells of the cells separated in Experimental Example 2, the cells were centrifuged at 600×g and 4° C. for 3 minutes. Subsequently, a base medium to which penicillin (a final concentration of 100 U/mL, Nacalai Tesque, cat. no. 26253-84), streptomycin (a final concentration of 100 μg/mL, Nacalai Tesque, cat. no. 26253-84), and amphotericin B (a final concentration of 0.25 μg/mL, Gibco, cat. no. 15240-062) were added was added to the obtained cell pellet, and the cell pellet was suspended so that a cell density became 5×10$^4$ cells/mL.

Subsequently, 200 μL of the cell suspension was seeded per insert, and 400 μL of a base medium containing an antibacterial drug was added to the well below the insert and 3D cultured. The medium was replaced with a base medium to which an antibacterial drug was not added every two to three days.

Figure 2:
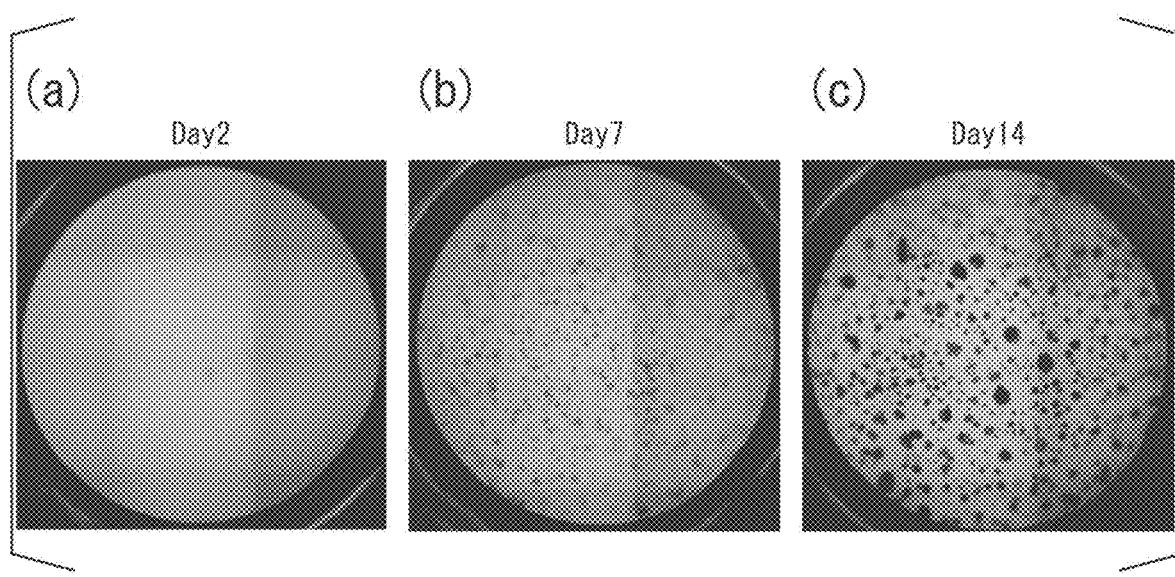
FIGS. 2(a) to 2(c) are photographs temporally showing an aspect in which $CD31^-CD45^-EpCAM^+$ lung cells were 3D cultured in Experimental Example 3.
Figure 3:
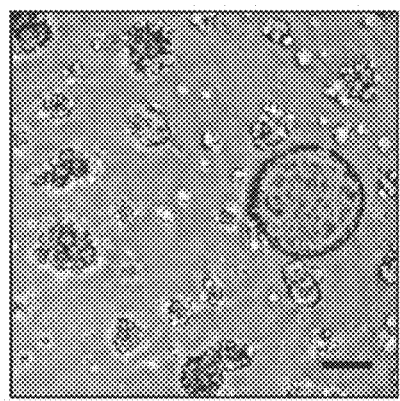
FIGS. 3(a) and 3(b) are photographs of an organoid formed as culturing of $CD31^-CD45^-EpCAM^+$ lung cells proceeds in Experimental Example 3.
Figure 3:
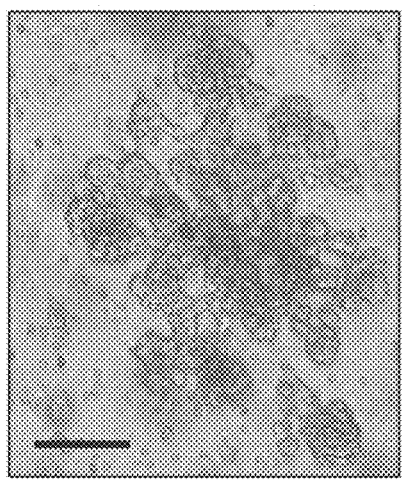

FIGS. 2(a) to 2(c) are photographs temporally showing an aspect in which CD31⁻CD45⁻EpCAM⁺ lung cells were cultured in three dimensions. FIG. 2(a) is a photograph two days after the start of culture, FIG. 2(b) is a photograph seven days after the start of culture, and FIG. 2(c) is a photograph fourteen days after the start of culture. In addition, FIGS. 3(a) and 3(b) are photographs of the organoid formed as culturing progressed. In FIGS. 3(a) and 3(b), a scale bar indicates 100 μm. As shown in FIGS. 3(a) and 3(b), organoids were formed in various forms by culture of the CD31⁻CD45⁻EpCAM⁺ lung cells in three dimensions.

Experimental Example 4

(Passage of CD31⁻CD45⁻EpCAM⁺ Lung Cell)
50 μL of Matrigel (Corning, cat. no. 356230) was put into a 0.4 μm cell culture insert (Falcon, cat. no. 353095) in advance, and allowed to stand at 37° C. for 30 minutes for gelation.

Subsequently, a medium of the insert where the cells reached confluence was removed, and 300 μL of collagenase/dispase (a final concentration of 1 mg/mL) was added thereto. The mixture was stirred and pipetted with a 1000 μL pipette to break up the gel, and a colony was recovered in a 1.5 mL tube.

Subsequently, the 1.5 mL tube was immersed in a 37° C. constant-temperature tank and allowed to stand for 20 minutes to dissolve the gel. Subsequently, the tube was centrifuged at 600×g at 4° C. for 3 minutes, the supernatant was removed, and 500 μL of 0.05% trypsin/EDTA (Gibco, cat. no. 15400-054) was added thereto. Pipetting was performed 50 to 60 times with a 200 μL pipette, and the tube was immersed in a 37° C. constant-temperature tank and allowed to stand for 10 minutes.

Thereafter, pipetting was performed again 50 to 60 times with a 200 μL pipette, the tube was immersed in a 37° C. constant-temperature tank and allowed to stand for 10 minutes, and 500 μL of Trypsin neutralizing solution (TNS, Lonza, cat. no. CC-5002) was added thereto.

Subsequently, the 1.5 mL tube was centrifuged at 600×g at 4° C. for 3 minutes, and the supernatant was removed to obtain a cell pellet. Subsequently, the obtained cell pellet was suspended in a base medium, 200 μL of the cell suspension was seeded per insert, and 400 μL of a base medium was added to the well below the insert and 3D cultured. The medium was replaced with a base medium every two to three days.

Experimental Example 5

(Analysis of Bronchioalveolar Stem Cell (BASC))
Primary culture, second passage, and third passage of the CD31⁻CD45⁻EpCAM⁺ lung cells cultured in Experimental Examples 3 and 4 were respectively analyzed with a flow cytometer.

The following were used as antibodies and coloring agents: PE-labeled anti-mouse Sca-1 antibody (Bio Legend, cat. no. 108107), PE-labeled rat IgG2b isotype control (eBioscience, cat. no. 12-4031-83), APC-labeled anti-mouse EpCAM rat monoclonal antibody (Bio Legend, cat. no. 118241), APC-labeled rat IgG2aκ isotype control (Bio Legend, cat. no. 400512), and PI (Sigma, no. P4170-10MG).

FIG. 4(a) is a graph showing results of analysis by flow cytometry of expression of EpCAM and Sca-1 in CD31⁻CD45⁻EpCAM⁺ lung cells of each of primary culture, second passage (passaged once, p1), and third passage (passaged twice, p2), with limitation to PI⁻CD31⁻CD45⁻ population or PI⁻ population. FIG. 4(b) is a graph collectively showing the results of FIG. 4(a).

As a result, it has become clear that, as the passage of the CD31⁻CD45⁻EpCAM⁺ lung cells proceeded by 3D culture using a serum-free medium, the number of bronchioalveolar stem cells (BASC) co-expressing EpCAM and Sca-1 significantly increased.

Experimental Example 6

(Fixation and Fluorescent Immunohistological Staining of Cultured CD31⁻CD45⁻EpCAM⁺ Lung Cell)
The CD31⁻CD45⁻EpCAM⁺ lung cells cultured in the same manner as in Experimental Examples 3 and 4 were fixed and subjected to fluorescent immunohistological staining. First, a medium of the insert where the cells reached confluence was removed, and 300 μL of collagenase/dispase (a final concentration of 1 mg/mL) was added thereto. Subsequently, the mixture was stirred and pipetted with a 1000 μL pipette of which a distal end was cut to break up the gel, and a colony was recovered in a 1.5 mL tube. Subsequently, the 1.5 mL tube was immersed in a 37° C. constant-temperature tank and allowed to stand for 20 minutes to dissolve the gel. Subsequently, the tube was centrifuged at 600×g at 4° C. for 3 minutes, the supernatant was removed, and the colony was embedded in a gel using iPGell (Genostuff, cat. no. PG20-1).

Subsequently, the gel in which the colony was embedded was immersed in 4% paraformaldehyde (Nacalai Tesque, cat. no. 09154-85) to fix the cells. Subsequently, paraffin-embedded blocks were produced, and sliced sections were produced. Subsequently, the sliced sections were attached to a slide glass. Subsequently, the antigen was activated by deparaffinization with xylene and heat treatment in 10 mM citric acid buffer (pH 6.0). Subsequently, blocking was performed with 3% bovine serum albumin (BSA)/PBS. Subsequently, as a primary antibody, rabbit anti-SPC polyclonal antibody (Santa Cruz, cat. no. sc-13979), and goat anti-CC10 monoclonal antibody (Santa Cruz, cat. no. sc-9772) were reacted at 4° C. over night. Subsequently, as a secondary antibody, goat anti-rabbit IgG-Alexa Flour 488 antibody (Life Technologies, cat. no. A11034) and donkey anti-goat IgG-Alexa Flour 594 antibody (Life Technologies, cat. no. A11034) were reacted at room temperature for 30 minutes, and then encapsulated using VECTASIELD MOUNTING MEDIUM with DAPI (Vector, cat. no. H-1200).

Figure 5:
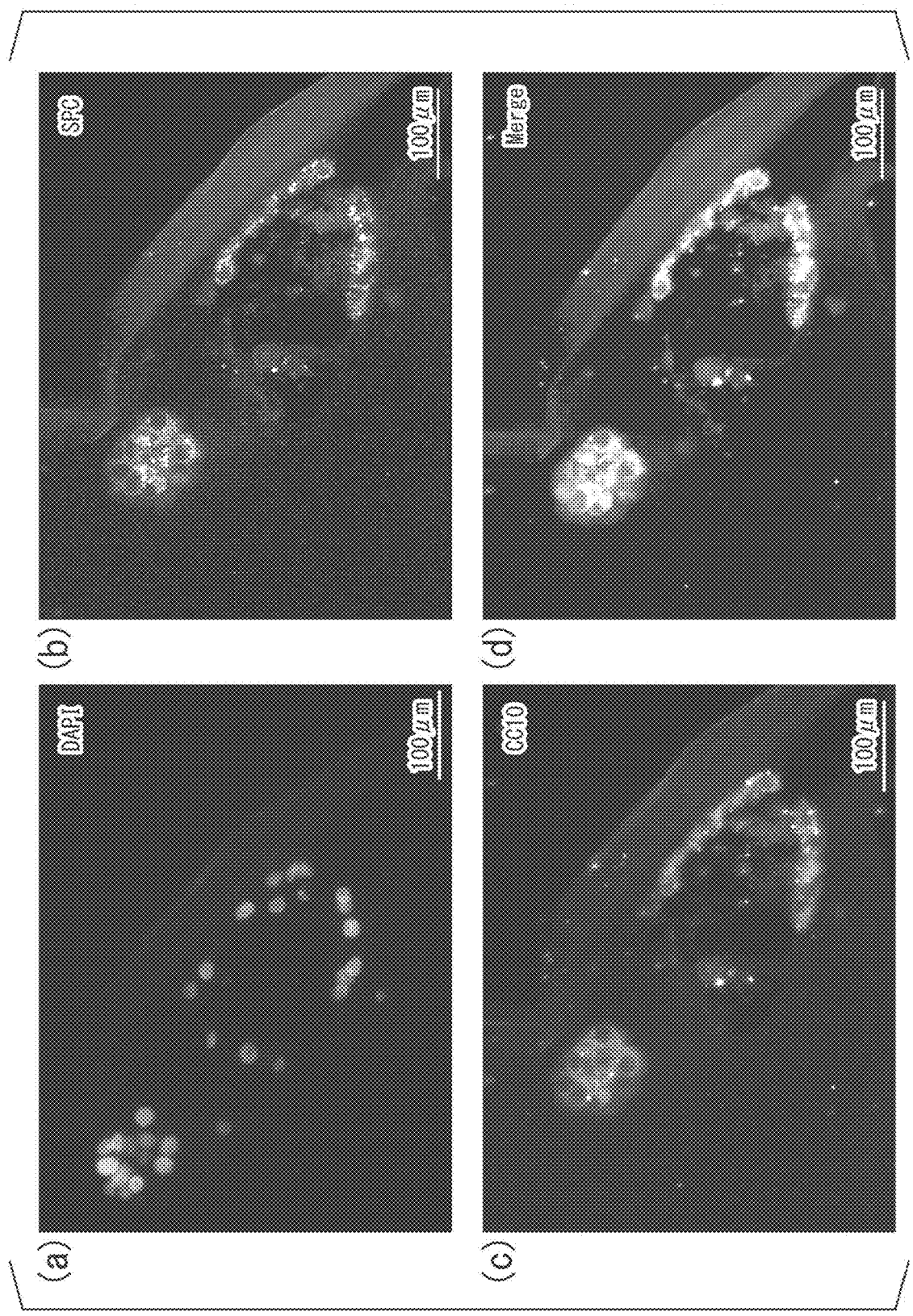
FIGS. 5(a) to 5(d) are fluorescence micrographs showing results of fluorescent immunohistological staining of cultured $CD31^-CD45^-EpCAM^+$ lung cells in Experimental Example 6.

FIGS. 5(a) to 5(d) are fluorescence micrographs of cells subject to fluorescent immunohistological staining. FIG. 5(a) is a fluorescence micrograph of the nucleus stained with DAPI. FIG. 5(b) is a fluorescence micrograph showing the localization of SPC. FIG. 5(c) is a fluorescence micrograph showing the localization of CC10. FIG. 5(d) is a photograph obtained by merging FIGS. 5(a) to 5(c). In FIGS. 5(a) to 5(d), the scale bar indicates 100 μm. As a result, it has become clear that the cell population in which the CD31⁻CD45⁻EpCAM⁺ lung cells were cultured includes the cells expressing SPC and CC10. As mentioned above, SPC and CC10 are markers of BASC. Accordingly, this result further supports that the CD31⁻CD45⁻EpCAM⁺ lung cells contain BASC.

Experimental Example 7

(Production of Retrovirus Expressing Oncogene)

Figure 4:
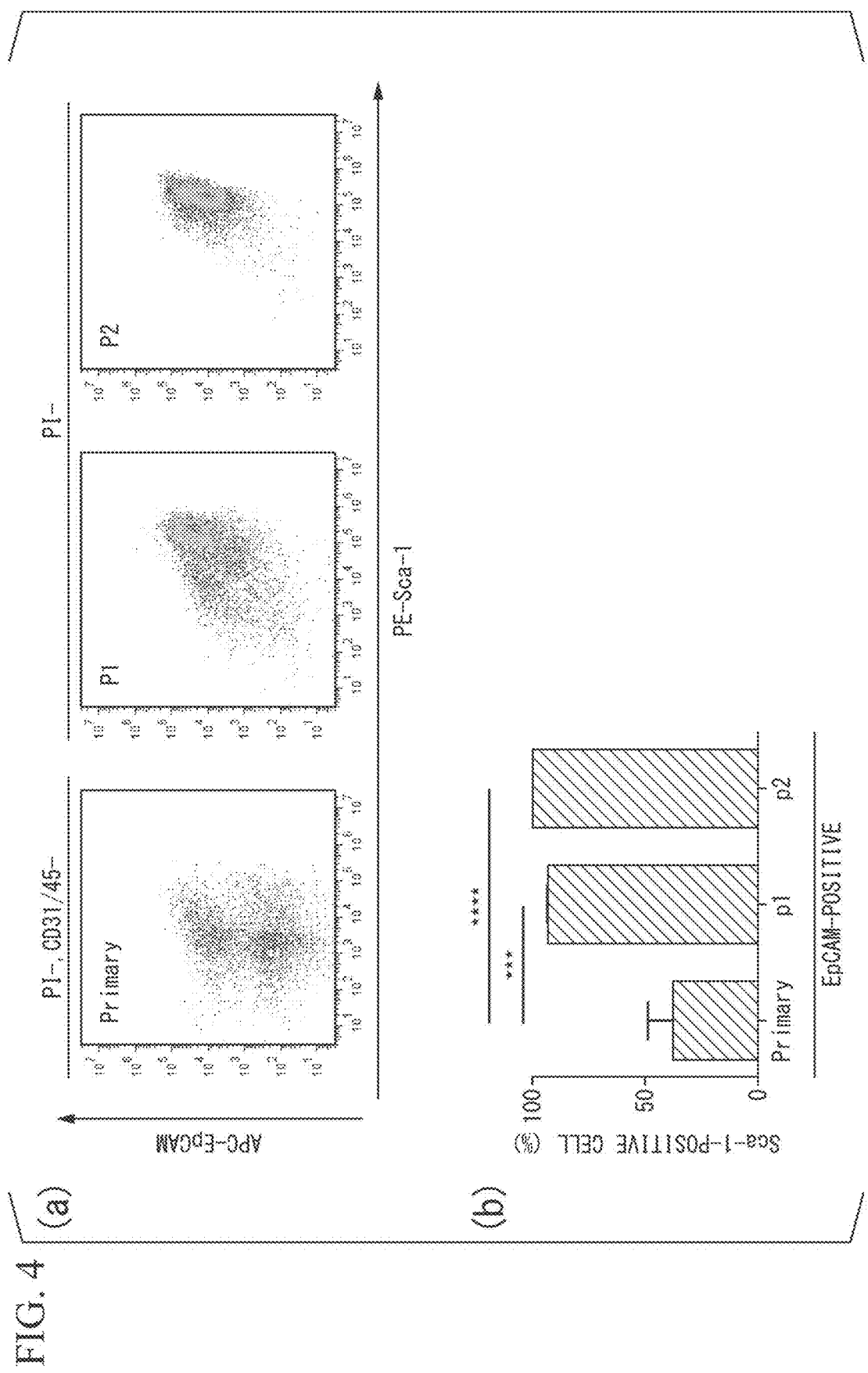
FIG. 4(a) is a graph showing results of analysis by flow cytometry of expression of EpCAM and Sca-1 in $CD31^-CD45^-EpCAM^+$ lung cells of each of primary culture, second passage (passaged once, p1), and third passage (passaged twice, p2) in Experimental Example 5.
FIG. 4(b) is a graph collectively showing the results of FIG. 4(a).
Figure 6:
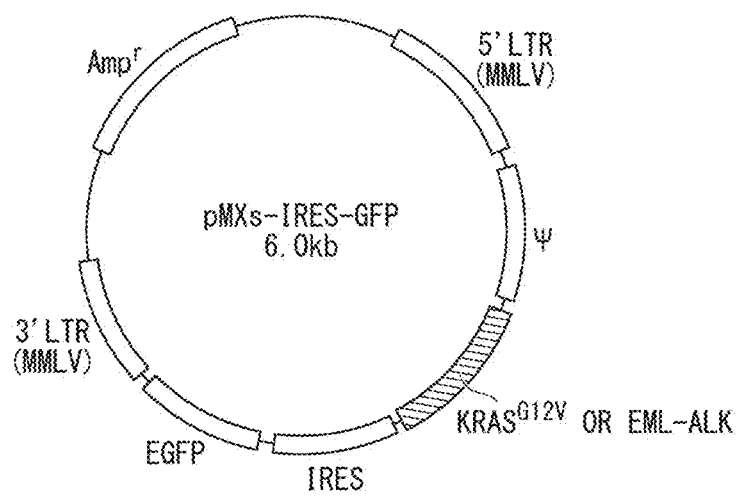
FIG. 6 is a view showing a structure of a retroviral vector plasmid produced in Experimental Example 7.

Retroviruses that express $KRAS^{G12V}$ and EML 4-ALK fusion genes, which are oncogenes, were produced. Specifically, first, GP2-293 cells, which are packaging cells, were seeded on two 10-cm culture dishes at a cell density of $4 \times 10^6$ cells/dish, respectively. Subsequently, after 4 to 6 hours, a retroviral vector plasmid (pMXs-$KRAS^{G12V}$-IRES-EGFP or pMXs-EML4-ALK-IRES-EGFP) and pVSV-G were transfected to GP2-293 cells using FuGENE HD (Promega, cat. no. E2312). The next day, the medium was replaced with DMEM (Nacalai Tesque, cat. no. 08459-64) containing 10% FBS. FIG. 4 shows a structure of a retroviral vector plasmid. As shown in FIG. 6, the EGFP gene was linked downstream of the $KRAS^{G12V}$ or EML4-ALK fusion gene, which are the oncogenes, via an internal ribosome entry site (IRES) sequence.

Subsequently, on the third day after transfection, the medium was recovered through a 0.45 μm filter (Iwaki, cat. no. 2053-025) in a 50 mL tube, and centrifuged at 23,000×g at 4° C. for 6 to 7 hours, and thereby a retroviral pellet was obtained. Subsequently, the supernatant was removed. The virus pellet was suspended in a base medium (not containing a ROCK inhibitor), transferred to a 1.5 mL tube, and stored at −80° C.

Experimental Example 8

(Introduction of Oncogene to Lung Cell)

50 μL of Matrigel (Corning, cat. no. 356230) was put into a 0.4 μm cell culture insert (Falcon, cat. no. 353095) in advance, and allowed to stand at 37° C. for 30 minutes for gelation.

Subsequently, the third to fourth passages of the CD31⁻CD45⁻EpCAM⁺ lung cells were pelleted in the same manner as in Experimental Example 4. Subsequently, 200 μL of the thawed virus solution produced in Experimental Example 7, a ROCK inhibitor (a final concentration of 10 mM), and protamine (a final concentration of 10 μg/mL, Sigma) were added to the obtained cell pellet, and the cell pellet was suspended so that a cell density became $1 \times 10^5$ cells/200 μL. Subsequently, 200 μL of the cell suspension was seeded per insert, and 400 μL of a base medium was added to the well below the insert and 3D cultured. The medium was changed to a base medium after 3 days. Thereafter, the medium was changed every 2 to 3 days.

12 to 14 days after virus infection, a cell pellet was obtained in the same manner as in Experimental Example 4. Subsequently, the cell pellet was suspended in a washing buffer to which PI (a final concentration of 0.1 μg/mL) was added, and GFP-positive cells were separated with a flow cytometer (type "MoFlo XDP flow cytometer," Beckman Coulter, Inc.).

The separated cells were suspended in 200 μl of a base medium and seeded on inserts. 400 μL of a base medium was also added to the well under the insert and cultured in three dimensions, and the medium was changed every 2 to 3 days. The cell colonies became confluent in about one week. The confluent cells were passaged in the same manner as in Experimental Example 4.

Figure 7:
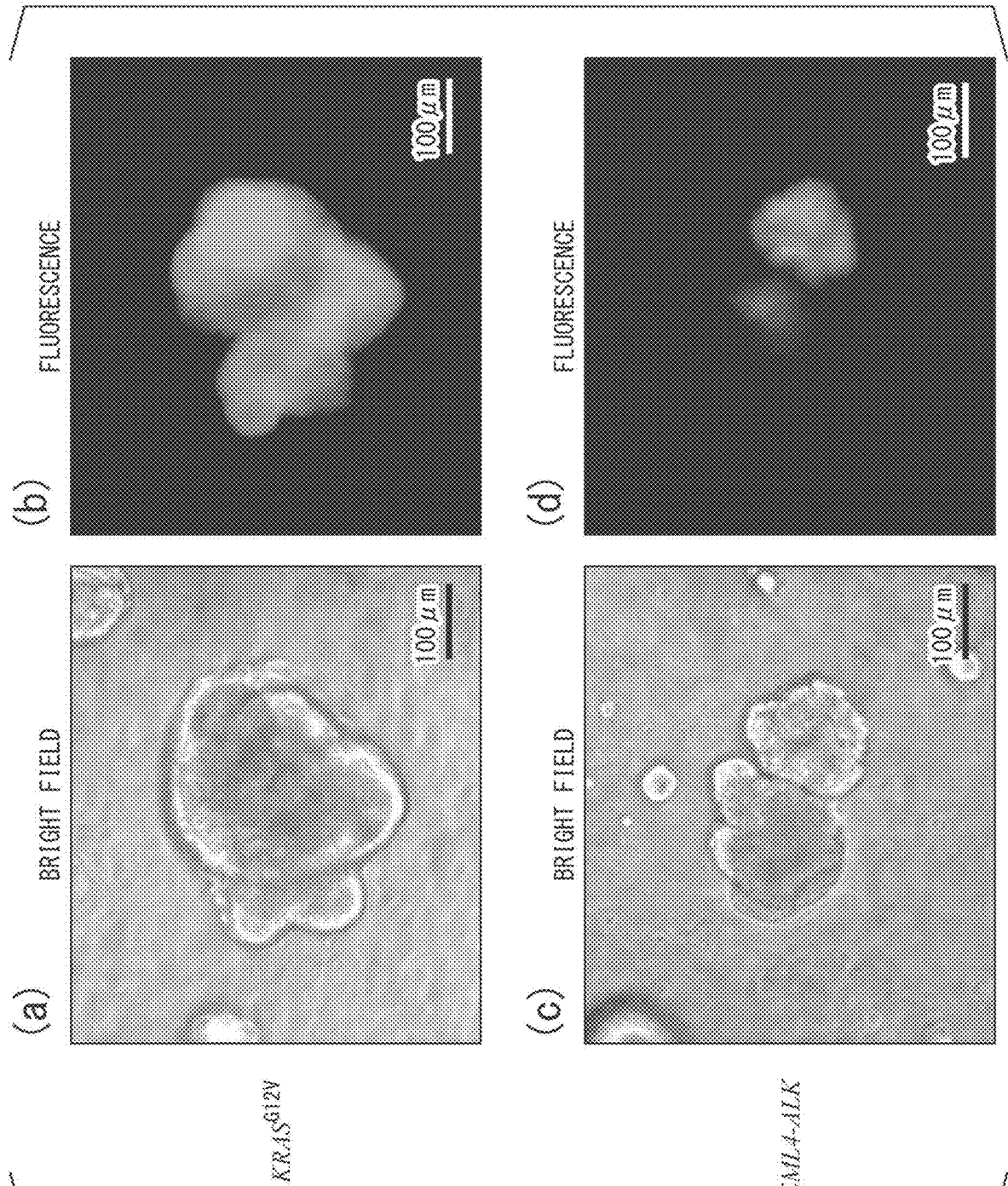
FIGS. 7(a) and 7(b) are photographs showing an example of an organoid formed as a result of 3D culture of lung cells into which $KRAS^{G12V}$, which is an oncogene, had been introduced in Experimental Example 8.
FIGS. 7(c) and 7(d) are photographs showing an example of an organoid formed as a result of 3D culture of lung cells into which EML4-ALK, which is an oncogene, had been introduced in Experimental Example 8.

FIGS. 7(a) and 7(b) are photographs showing an example of an organoid formed as a result of 3D culture of lung cells into which $KRAS^{G12V}$, which is an oncogene, had been introduced. FIG. 7(a) is a photograph in bright field, and FIG. 7(b) is a photograph in which fluorescence of GFP is observed in the same field of view as FIG. 7(a).

FIGS. 7(c) and 7(d) are photographs showing an example of an organoid formed as a result of 3D culture of lung cells into which EML4-ALK fusion gene had been introduced. FIG. 7(c) is a photograph in bright field, and FIG. 7(d) is a photograph in which fluorescence of GFP is observed in the same field of view as FIG. 7(c).

Experimental Example 9

(Transplantation (Subcutaneously) of Lung Cell into which Oncogene is Introduced to Mouse)

The lung cells into which the oncogene, $KRAS^{G12V}$ was introduced and which was produced in Experimental Example 8 were transplanted subcutaneously to a wild-type C57BL/6J mouse. Specifically, first, a medium of the insert where the cells reached confluence was removed, 300 μL of collagenase/dispase (a final concentration of 1 mg/mL) was added thereto. The mixture was stirred and pipetted with a 1000 μL pipette to break up the gel, and a colony was recovered in a 1.5 mL tube.

Subsequently, the 1.5 mL tube was immersed in a 37° C. constant-temperature tank and allowed to stand for 20 minutes to dissolve the gel. Subsequently, the tube was centrifuged at 600×g at 4° C. for 3 minutes, the supernatant was removed, and 500 μL of 0.05% trypsin/EDTA (Gibco, cat. no. 15400-054) was added thereto. Pipetting was performed 50 to 60 times with a 200 μL pipette, and the tube was immersed in a 37° C. constant-temperature tank and allowed to stand for 10 minutes.

Thereafter, pipetting was performed again 50 to 60 times with a 200 μL pipette, the tube was immersed in a 37° C. constant-temperature tank and allowed to stand for 10 minutes, and 500 μL of Trypsin neutralizing solution (TNS, Lonza, cat. no. CC-5002) was added thereto.

Subsequently, the 1.5 mL tube was centrifuged at 600×g at 4° C. for 3 minutes, and the supernatant was removed to obtain a cell pellet. Subsequently, the obtained cell pellet was suspended in PBS. The suspension was mixed with the Matrigel dissolved on ice in advance at 1:1, and a cell density was adjusted to $5 \times 10^5$ cells/100 μL. Subsequently, the back of the wild-type C57BL6/J mouse was shaved, and 100 μL of the cell suspension was injected subcutaneously at each one site of right and left sides.

After breeding for 3 weeks from cell transplantation, tumor formation was observed, and a cancer-bearing mouse model was obtained. Subsequently, the tumor was excised from the cancer-bearing mouse model, and analyzed by immunohistochemical staining.

Specifically, first, the excised tumor tissue was fixed with 4% paraformaldehyde (Nacalai Tesque, cat. no. 09154-85). Subsequently, paraffin-embedded blocks were produced, and sliced sections were produced. Subsequently, the sliced sections were attached to a slide glass. Subsequently, the antigen was activated by deparaffinization with xylene and heat treatment in 10 mM citric acid buffer (pH 6.0). Subsequently, endogenous peroxidase activity was inhibited by immersion in 3% hydrogen peroxide/PBS. Subsequently, blocking was performed with 3% bovine serum albumin (BSA)/PBS.

Subsequently, as a primary antibody, rabbit anti-GFP polyclonal antibody (Santa Cruz, cat. no. sc-8334) or rabbit anti-TTF-1 monoclonal antibody (Abcam, cat. no. ab76013) was reacted at 4° C. over night. Thyroid transcription factor-1 (TTF-1) is a transcription factor involved in development of thyroid and lung and is also a marker for lung adenocarcinoma.

Subsequently, as a secondary antibody, a biotin-labeled goat anti-rabbit IgG antibody (Vector, cat. no. PK-6101) was reacted at room temperature for 30 minutes.

Subsequently, VECTASTAIN Elite ABC (Vector, cat. no. PK-6101) was reacted at room temperature for 30 minutes, and then ImmPACT DAB (Vector, cat. no. SK-4105) was reacted to develop color.

Figure 8:
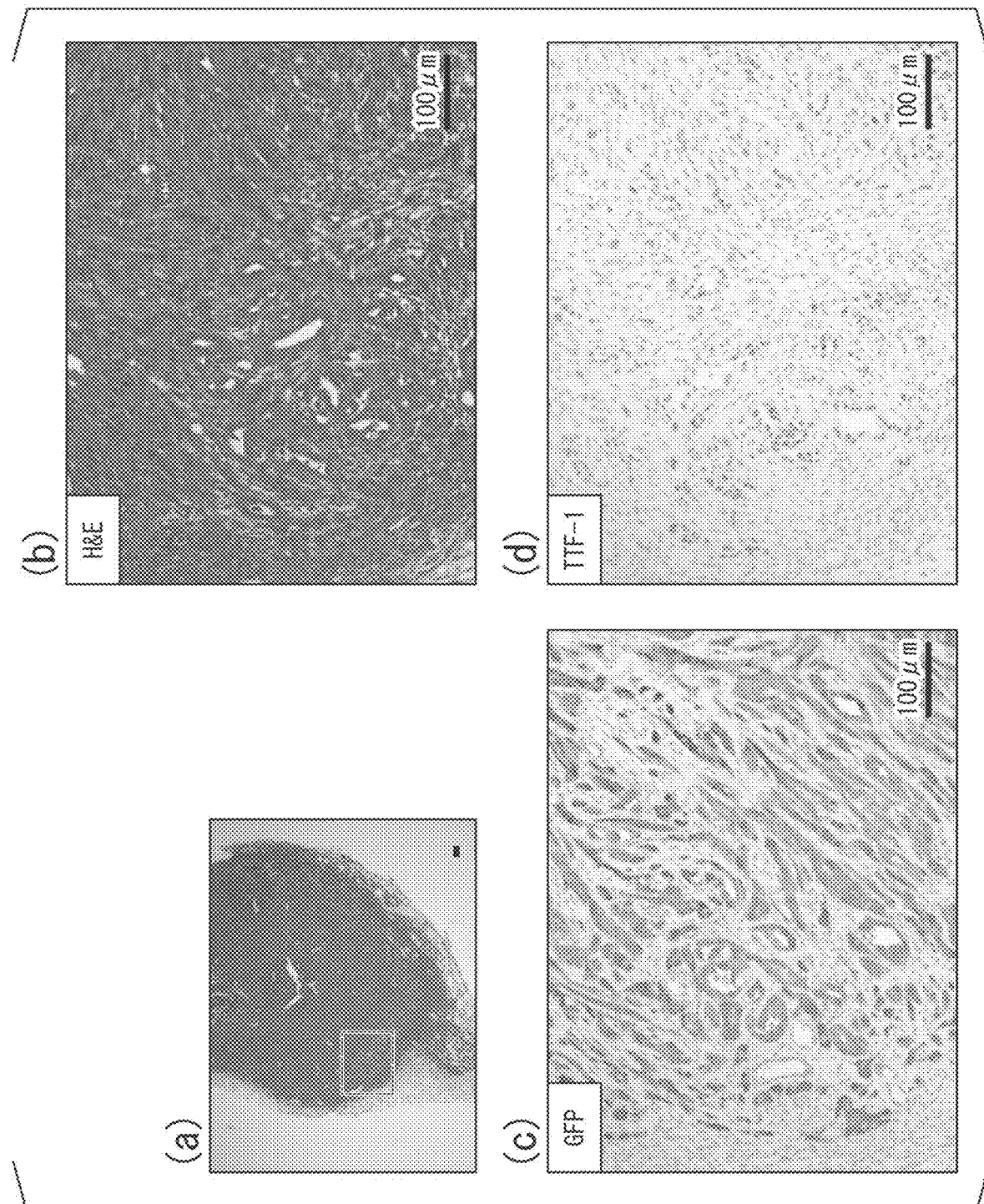
FIGS. 8(a) to 8(d) are photographs showing results of immunohistochemical staining in Experimental Example 9.

FIG. 8(a) is a micrograph showing results of hematoxylin-eosin staining of a sliced section of a tumor tissue. The scale bar is 100 µm. In addition, FIG. 8(b) is an enlarged micrograph of a boxed area of FIG. 8(a). As a result, it has become clear that the lung cells into which the oncogene had been introduced form a tumor of a histologic type of differentiated adenocarcinoma which is often observed in human lung adenocarcinomas such as acinar-type tumors and papillary-type tumors, even in a subcutaneous environment. These tumors are histologic types that are extremely rarely observed in transplanted lung cancer models obtained by techniques of the related art. Based on these results, it has become clear that the method of the present experimental example is remarkably superior as a method for producing a cancer-bearing non-human animal model closer to a human.

FIG. 8(c) is a micrograph showing results of staining a sliced section of a tumor tissue with an anti-GFP antibody, and FIG. 8(d) is a micrograph showing results of staining a sliced section of a tumor tissue with an anti-TTF-1 antibody. As a result, it has become clear that expression of TTF-1, which is a lung differentiation marker and lung adenocarcinoma marker, is positive.

Experimental Example 10

(Transplantation (To Subcapsular Kidney) of Lung Cell into which Oncogene is Introduced to Mouse)

The lung cells into which the oncogene, $KRAS^{G12V}$ was introduced and which was produced in Experimental Example 8 were transplanted to a subcapsular kidney of a wild-type C57BL/6J mouse. Specifically, first, a medium of the insert where the cells reached confluence was removed, 300 µL of collagenase/dispase (a final concentration of 1 mg/mL) was added thereto. The mixture was stirred and pipetted with a 1000 µL pipette to break up the gel, and a colony was recovered in a 1.5 mL tube.

Subsequently, the 1.5 mL tube was immersed in a 37° C. constant-temperature tank and allowed to stand for 20 minutes to dissolve the gel. Subsequently, the tube was centrifuged at 600×g at 4° C. for 3 minutes, the supernatant was removed, and 500 µL of 0.05% trypsin/EDTA (Gibco, cat. no. 15400-054) was added thereto. Pipetting was performed 50 to 60 times with a 200 µL pipette, and the tube was immersed in a 37° C. constant-temperature tank and allowed to stand for 10 minutes.

Thereafter, pipetting was performed again 50 to 60 times with a 200 µL pipette, the tube was immersed in a 37° C. constant-temperature tank and allowed to stand for 10 minutes, and 500 µL of Trypsin neutralizing solution (TNS, Lonza, cat. no. CC-5002) was added thereto.

Subsequently, the 1.5 mL tube was centrifuged at 600×g at 4° C. for 3 minutes, and the supernatant was removed to obtain a cell pellet. Subsequently, the obtained cell pellet was suspended in PBS. Subsequently, the back of the wild-type C57BL6/J mouse was shaved under anesthesia, the back skin was incised, the kidney was pulled and exposed to the body surface, and a 27-gauge needle was inserted from a lower pole to an upper pole direction. Subsequently, the needle was once removed, and 10 µL of a cell suspension was injected to the subcapsular kidney of an upper pole with a 200 µL tip. After this operation was performed on both kidneys, the peritoneal membrane and skin were sutured.

After breeding for 5 weeks from cell transplantation, tumor formation was observed, and a cancer-bearing mouse model was obtained. Subsequently, the tumor was excised from the cancer-bearing mouse model, and analyzed by immunohistochemical staining in the same manner as in Experimental Example 9.

Figure 9:
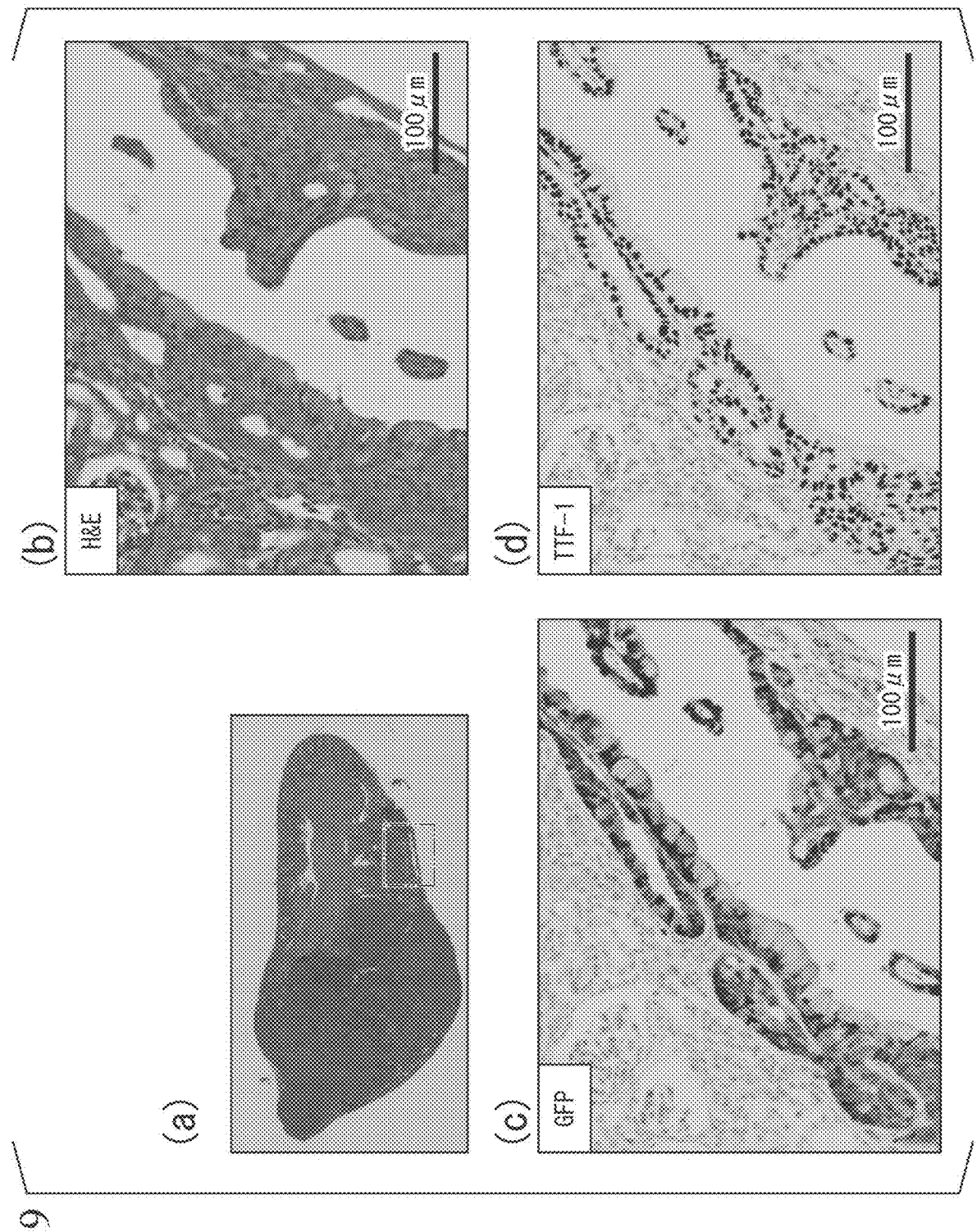
FIGS. 9(a) to 9(d) are photographs showing results of immunohistochemical staining in Experimental Example 10.

FIG. 9(a) is a micrograph showing results of hematoxylin-eosin staining of a sliced section of a tumor tissue. The scale bar is 100 µm. In addition, FIG. 9(b) is an enlarged micrograph of a boxed area of FIG. 9(a). As a result, it has become clear that the lung cells into which the oncogene had been introduced form a tumor of a histologic type which is often observed in human lung adenocarcinomas called mucin-producing acinar-type tumor, even in a subcapsular kidney environment.

FIG. 9(c) is a micrograph showing results of staining a sliced section of a tumor tissue with an anti-GFP antibody, and FIG. 9(d) is a micrograph showing results of staining a sliced section of a tumor tissue with an anti-TTF-1 antibody. As a result, it has become clear that expression of TTF-1, which is a lung differentiation marker and lung adenocarcinoma marker, is positive.

Experimental Example 11

(Transplantation (Subcutaneously) of Lung Cell into which Fusion Gene is Introduced to Mouse)

The lung cells into which the EML4-ALK fusion gene was introduced and which was produced in Experiment Example 8 were subcutaneously transplanted to a wild-type C57BL/6J mouse in the same manner as in Experiment Example 9.

After breeding for 5 weeks from cell transplantation, tumor formation was observed, and a cancer-bearing mouse model was obtained. Subsequently, the tumor was excised from the cancer-bearing mouse model, and analyzed by immunohistochemical staining in the same manner as in Experimental Example 9.

Figure 10:
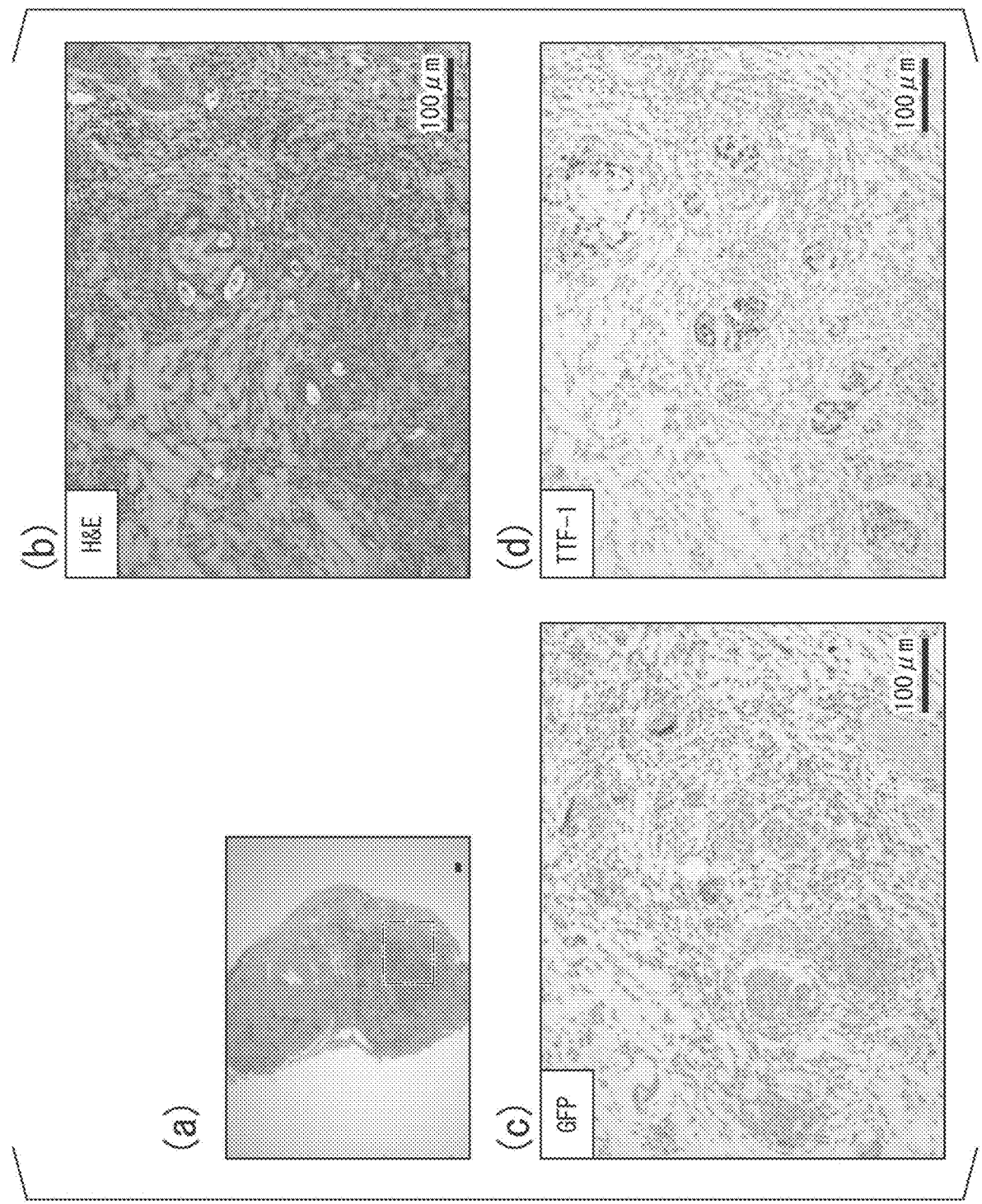
FIGS. 10(a) to 10(d) are photographs showing results of immunohistochemical staining in Experimental Example 11.

FIG. 10(a) is a micrograph showing results of hematoxylin-eosin staining of a sliced section of a tumor tissue. The scale bar is 100 µm. In addition, FIG. 10(b) is an enlarged micrograph of a boxed area of FIG. 10(a). As a result, it has become clear that the lung cells into which the oncogene had been introduced form a tumor of a histologic type which is often observed in human lung adenocarcinomas called mucin-producing acinar-type tumor, even in a subcutaneous environment.

FIG. 10(c) is a micrograph showing results of staining a sliced section of a tumor tissue with an anti-GFP antibody, and FIG. 10(d) is a micrograph showing results of staining a sliced section of a tumor tissue with an anti-TTF-1 antibody. As a result, it has become clear that expression of TTF-1, which is a lung differentiation marker and lung adenocarcinoma marker, is positive.

Experimental Example 12

(Transplantation (To Lung) of Lung Cell into which Oncogene is Introduced to Mouse)

The lung cells into which an oncogene was introduced and which was produced in Experimental Example 8 were transplanted to the lungs of a wild-type C57BL/6J mouse to produce a cancer-bearing mouse model, and tumor tissues were analyzed immunohistochemically. Bleomycin 0.025 U was intratracheally administered to the C57BL/6J mouse 10 to 14 days prior to cell transplantation.

As a result, even in a case where the lung cells into which an oncogene had been introduced were transplanted into the lung, the same results as in Experimental Examples 9 to 11 were obtained. In other words, a tumor of a histologic type which is often observed in human lung adenocarcinomas such as acinar-type tumors and papillary-type tumors was observed, and it has become clear that expression of TTF-1, which is a lung differentiation marker and lung adenocarcinoma marker, is positive.

Experimental Example 13

(Examination of Lung Cell Obtained by Introducing Oncogene into Cell in which Tumor Suppressor Gene is Normal)

Cells were cultured in the same manner as in Experimental Examples 2 to 4 and 8 except that the CD31$^-$CD45$^-$EpCAM$^+$ lung cells were separated from the wild-type C57BL6/J mouse, and the oncogene, KRAS$^{G12V}$ was introduced thereinto. However, lung cells obtained by isolating the CD31$^-$CD45$^-$EpCAM$^+$ lung cells from the mouse having a normal tumor suppressor gene, and introducing the oncogene, KRAS$^{G12V}$ thereinto did not proliferate, and therefore establishment of cell lines and transplantation into a mouse could not be performed.

This result indicates that, in order to produce a cancer-bearing mouse model, it is necessary to introduce an oncogene into cells in which a tumor suppressor gene has been deleted, and to transplant the cells.

Experimental Example 14

(Crizotinib Treatment Experiment Using Cancer-Bearing Mouse Model)

The lung cells into which the oncogene, EML4-ALK fusion gene was introduced and which was produced in Experimental Example 8 were transplanted subcutaneously on the back of an athymic mouse, and thereby a cancer-bearing mouse model was produced. Specifically, first, a medium of the insert where the cells reached confluence was removed, 300 µL of collagenase/dispase (a final concentration of 1 mg/mL) was added thereto. The mixture was stirred and pipetted with a 1000 µL pipette to break up the gel, and a colony was recovered in a 1.5 mL tube.

Subsequently, the 1.5 mL tube was immersed in a 37° C. constant-temperature tank and allowed to stand for 20 minutes to dissolve the gel. Subsequently, the tube was centrifuged at 600×g at 4° C. for 3 minutes, the supernatant was removed, and 500 µL of 0.05% trypsin/EDTA (Gibco, cat. no. 15400-054) was added thereto. Pipetting was performed 50 to 60 times with a 200 µL pipette, and the tube was immersed in a 37° C. constant-temperature tank and allowed to stand for 10 minutes.

Thereafter, pipetting was performed again 50 to 60 times with a 200 µL pipette, the tube was immersed in a 37° C. constant-temperature tank and allowed to stand for 10 minutes, and 500 µL of Trypsin neutralizing solution (TNS, Lonza, cat. no. CC-5002) was added thereto.

Subsequently, the 1.5 mL tube was centrifuged at 600×g at 4° C. for 3 minutes, and the supernatant was removed to obtain a cell pellet. Subsequently, the obtained cell pellet was suspended in PBS. The suspension was mixed with the Matrigel dissolved on ice in advance at 1:1, and a cell density was adjusted to 5×10$^6$ cells/100 µL.

Subsequently, 100 µL of the cell suspension was subcutaneously injected into the back of the athymic mouse at one site.

Subsequently, after breeding for 28 days from cell transplantation, tumor formation was observed, and a cancer-bearing mouse model was obtained.

Subsequently, crizotinib (150 mg/kg, Pfizer), which is a type of an anticancer agent, was orally administered for 14 consecutive days to an individual whose tumor formation could be confirmed. In addition, as a control, a group in which methylcellulose (Wako, cat. no. 131-17811) was orally administered for 14 consecutive days was prepared. A tumor volume of a mouse of each group was measured over time.

Figure 11:
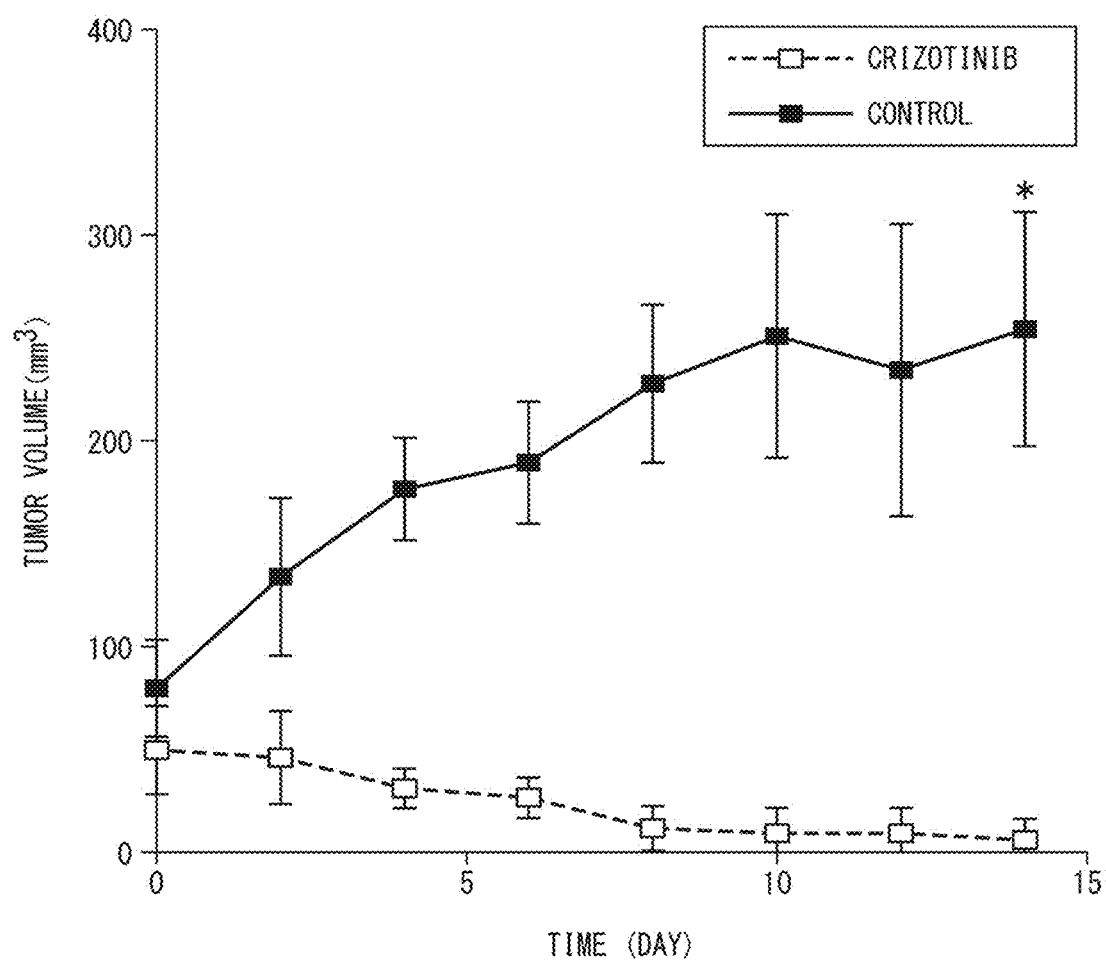
FIG. 11 is a graph showing measurement results of a tumor volume of a cancer-bearing mouse model in Experimental Example 14.

FIG. 11 is a graph showing measurement results of a tumor volume of a mouse of each group (n=3). In FIG. 11, the graph shows mean value±standard error. In addition, a lateral axis indicates a time (day) from the start of administration of crizotinib or methylcellulose. Furthermore, the symbol "*" indicates that there is a significant difference at P<0.05 by Student's t-test. As a result, it has become clear that tumor growth was significantly suppressed in the crizotinib-administered group.

Experimental Example 15

(Analysis of Sca-1 and Ly6D Expression in Lung Cell)

Cells from primary culture and the third passage of CD31$^-$CD45$^-$EpCAM$^+$ lung cells collected from a wild-type mouse, cells from primary culture and the second passage of CD31$^-$CD45$^-$EpCAM$^+$ lung cells collected from an Ink4a/Arf$^{-/-}$ C57BL/6J mouse, and lung cells into which KRAS$^{G12V}$ or EML4-ALK was introduced, were respectively analyzed with a flow cytometer. All cells were three-dimensionally cultured using a serum-free medium.

The following were used as antibodies and coloring agents: PE-Cy7-labeled anti-mouse Sca-1 antibody (Biolegend, cat. no. 122513), PE-Cy7-labeled rat IgG2a isotype control (Biolegend, cat. no. 400521), PE-labeled anti-mouse Ly6D antibody (Bio Legend, cat. no. 138603), PE-labeled rat IgG2b isotype control, APC-labeled anti-mouse EpCAM rat monoclonal antibody, APC-labeled rat IgG2aκ isotype control, and PI (Sigma, no. P4170-10MG).

Figure 12:
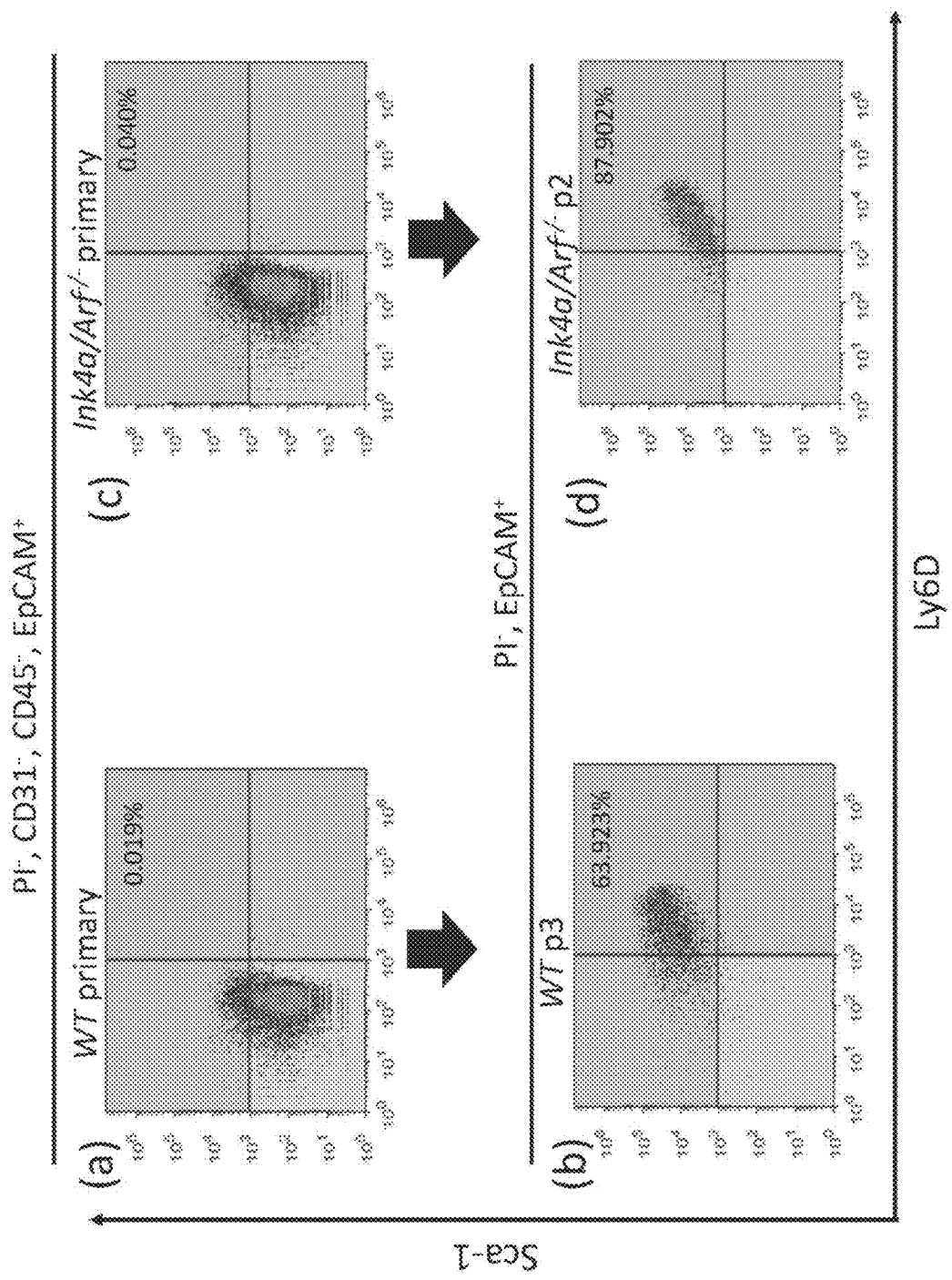
FIGS. 12(a) and 12(b) are graphs showing results of analysis by flow cytometry of expression of Sca-1 and Ly6D in $CD31^-CD45^-EpCAM^+$ lung cells, which were collected from a wild-type mouse, of each of primary culture and third passage in Experimental Example 15.
FIGS. 12(c) and 12(d) are graphs showing results of analysis by flow cytometry of expression of Sca-1 and Ly6D in $CD31^-CD45^-EpCAM^|$ lung cells, which were collected from an $Ink4a/Arf^{-/-}$ C57BL6/J mouse, of each of primary culture and second passage in Experimental Example 15.

FIGS. 12(a) and 12(b) are graphs showing results of analysis by flow cytometry of expression of Sca-1 and Ly6D in CD31$^-$CD45$^-$EpCAM$^+$ lung cells, which were collected from a wild-type mouse, of each of primary culture and the third passage, with limitation to PI$^-$CD31$^-$CD45$^-$EpCAM$^+$ population or PI$^-$EpCAM$^+$ population.

FIGS. 12(c) and 12(d) are graphs showing results of analysis by flow cytometry of expression of Sca-1 and Ly6D in CD31$^-$CD45$^-$EpCAM$^+$ lung cells, which were collected from an Ink4a/Arf$^{-/-}$ C57BL/6J mouse, of each of primary culture and the second passage, with limitation to PI$^-$CD31$^-$CD45$^-$EpCAM$^+$ population or PI$^-$EpCAM$^+$ population.

Figure 13:
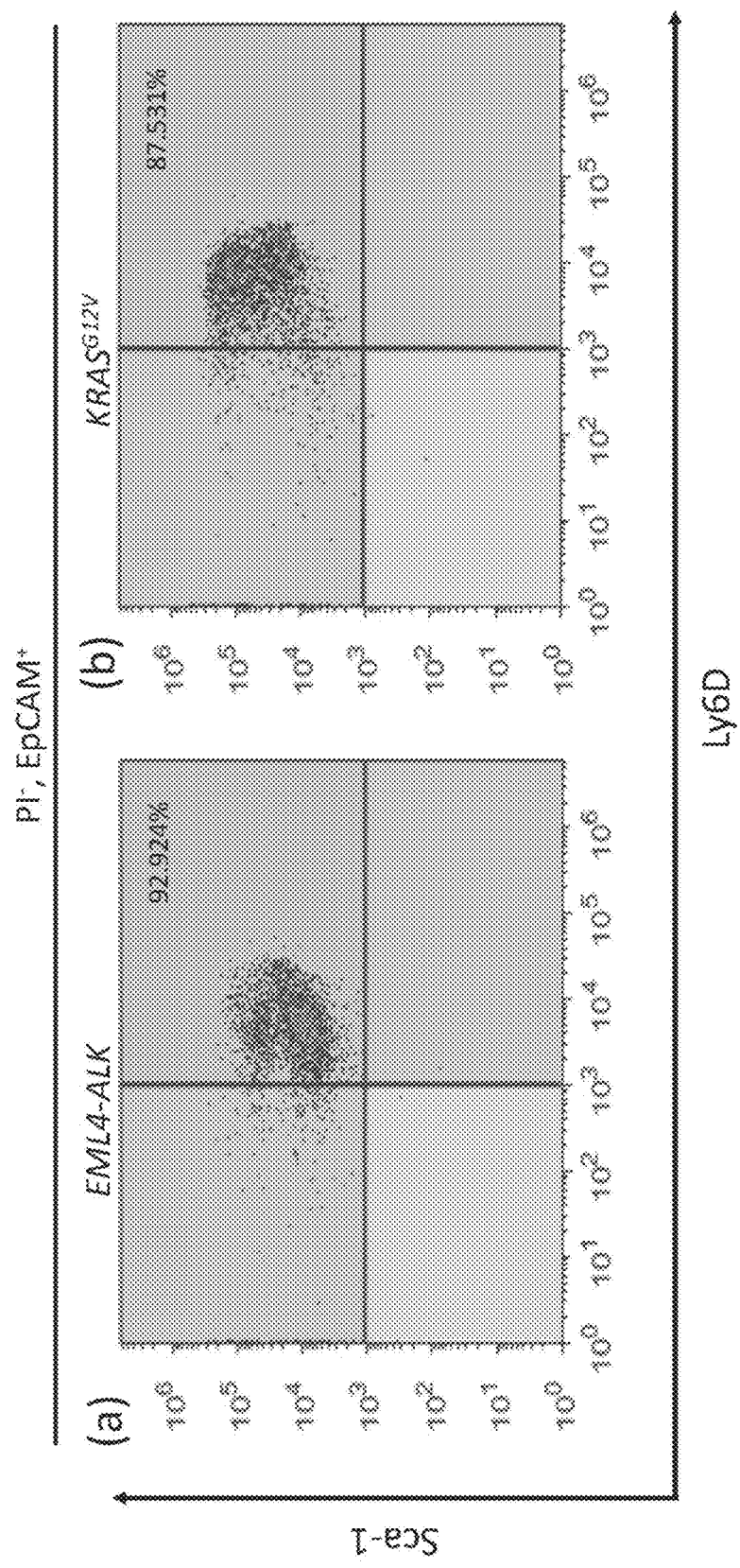
FIGS. 13(a) and 13(b) are graphs showing results of analysis by flow cytometry of expression of Sca-1 and Ly6D in each of cells obtained by introducing KRAS$^{G12V}$ or EML4-ALK into CD31$^-$CD45$^-$EpCAM$^+$ lung cells collected from an Ink4a/Arf$^{-/-}$ C57BL6/J mouse in Experimental Example 15.

FIGS. 13(a) and 13(b) are graphs showing results of analysis by flow cytometry of expression of Sca-1 and Ly6D in each of cells obtained by introducing KRAS$^{G12V}$ or EML4-ALK into CD31$^-$CD45$^-$EpCAM$^+$ lung cells collected from an Ink4a/Arf$^{-/-}$ C57BL/6J mouse, with limitation to PI$^-$EpCAM$^+$ population.

As a result, it has become clear that, by 3D culture using a serum-free medium, expression of Ly6D was increased as in the case of Sca-1, and the expression was maintained even after oncogene introduction.

Experimental Example 16

(Separation of Cell and Tissue of Liver, Gallbladder, Extrahepatic Bile Duct of Ink4a/Arf$^{-/-}$ Mouse)

Cultured epithelial cells lacking at least one tumor suppressor gene were prepared from tissues other than lung.

Specifically, liver, gallbladder, and extrahepatic bile duct were isolated from an Ink4a/Arf$^{-/-}$ mouse.

First, 0.3 mL of pentobarbital (a final concentration of 7.2 mg/mL, Kyoritsu Seiyaku, cat. no. SOM02-YA1312) per mouse was intraperitoneally injected to the Ink4a/Arf$^{-/-}$ C57BL6/J mice for anesthetization.

Subsequently, the mouse was fixed in a supine position, the skin was incised in midline from the lower abdomen to the epigastric region, and the skin was exfoliated to right and left sides. Subsequently, the peritoneal membrane was incised in a T-shape along the median and calcaneal arch to expose the liver, and discussion of the hepatic falciform ligament attached to the diaphragm was performed. Subsequently, the liver was displaced to the diaphragm side to expose the stomach, duodenum, and hepatoduodenal ligament. Subsequently, the extrahepatic bile duct in the hepatoduodenal ligament was exposed, and the extrahepatic bile duct from the upper border of the pancreas to the hepatic portal region was excised. Subsequently, the gallbladder was exfoliated and exposed to the gallbladder duct, and the gallbladder was excised. Subsequently, the inferior vena cava and the superior vena cava below the diaphragm were cut off, and the liver, together with the right hepatic lobe, the medial lobe, the quadrate lobe, and the left lobe, was excised.

Subsequently, the respective excised liver, gallbladder, and extrahepatic bile duct were minced with scissors. Thereafter, the minced organs were transferred to a conical tube to which DMEM/Ham's F-12 with L-glutamine (Wako, cat. no. 048-29785) supplemented with Collagenase D (a final concentration of 2 mg/mL, Roche, cat. no. 11088866001), Dispase II (a final concentration of 0.125 mg/mL, Thermo Fisher, cat. no. 17105041), and DNase I (a final concentration of 0.1 mg/mL, Sigma-Aldrich, cat. no. DN25-100MG) were put, and shaken at 37° C. for 45 minutes.

Subsequently, after allowing the cells to pass through a 100 µm cell strainer (Falcon, cat. no. 352360), the cells were allowed to pass through a 40 µm cell strainer (Falcon, cat. no. 352340).

Subsequently, after centrifuging at 300×g for 5 minutes and removing the supernatant, 10 mL of TripLETM (Gibco, cat. no. 12604021) supplemented with DNase I (a final concentration of 0.1 mg/mL, Sigma-Aldrich, cat. no. DN25-100MG) was put into the tube, and shaken at 37° C. for 5 minutes. Subsequently, the cells were allowed to pass through a 40 µm cell strainer (Falcon, cat. no. 352340). Subsequently, after centrifuging at 300×g for 5 minutes and removing the supernatant, 10 mL of erythrocyte hemolysis buffer supplemented with DNase I (a final concentration of 0.1 mg/mL, Sigma-Aldrich, cat. no. DN25-100MG) was added, and the mixture was allowed to stand at 4° C. for 5 minutes.

Subsequently, centrifugation was performed at 300×g for 5 minutes. Subsequently, after removing the supernatant, the cells were suspended in 10% FBS/PBS (a washing buffer) supplemented with DNase I (a final concentration of 0.1 mg/mL, Sigma-Aldrich, cat. no. DN25-100MG), Y27632 (a final concentration of 10 µM, Miltenyi Biotech, cat. no. 130-106-538), Penicillin (a final concentration of 100 U/mL, Nacalai Tesque, cat. no. 26253-84), Streptomycin (a final concentration of 100 µg/mL, Nacalai Tesque, cat. no. 26253-84), and Amphotericin B (a final concentration of 0.25 µg/mL, Gibco, cat. no. 15240-062). The cells were allowed to pass through a 40 µm cell strainer (Falcon, cat. no. 352340), and thereby cells each derived from the liver, gallbladder, and extrahepatic bile duct were obtained.

Experimental Example 17

(Separation of CD31$^-$CD45$^-$EpCAM$^+$ Bile Duct Epithelial Cell and Gallbladder Epithelial Cell)

CD31$^-$CD45$^-$EpCAM$^+$ bile duct epithelial cells and CD31$^-$CD45$^-$EpCAM$^+$ gallbladder epithelial cells were respectively isolated from the bile duct epithelial cells and the gallbladder epithelial cells prepared in Experimental Example 16, by using a flow cytometer (type "MoFlo XDP flow cytometer," Beckman Coulter, Inc.).

The following were used as antibodies and coloring agents: FITC-labeled anti-mouse CD31 rat monoclonal antibody (Bio Legend, cat. no. 102406), FITC-labeled anti-mouse CD45 rat monoclonal antibody (Bio Legend, cat. no. 103108), FITC-labeled rat IgG2b isotype control (Bio Legend, cat. no. 400505), APC-labeled anti-mouse CD326 (EpCAM) rat monoclonal antibody (Bio Legend, cat. no. 118214), APC-labeled rat IgG2aк isotype control (Bio Legend, cat. no. 400512), and PI (Sigma, no. P4170-10MG).

Experimental Example 18

(Culture of CD31$^-$CD45$^-$EpCAM$^+$ Bile Duct Epithelial Cell and Gallbladder Epithelial Cell)

50 µL of Matrigel (Corning, cat. no. 356230) was put into a 0.4 µm cell culture insert (Falcon, cat. no. 353095) in advance, and allowed to stand at 37° C. for 30 minutes for gelation.

As a base medium, DMEM/Ham's F-12 with L-glutamine (Wako, cat. no. 048-29785), Hepatocyte growth factor (a final concentration of 50 ng/mL, Biolegend, cat. no. 596402), Epidermal growth factor (a final concentration of 50 ng/mL, Peprotech, cat. no. AF-100-15), Fibroblast growth factor 10 (a final concentration of 100 ng/mL, Bio Legend, cat. no. 559302), R-spondin 1 (a final concentration of 0.5 µg/mL, Miltenyi Biotech, cat. no. 130-105-799), Nicotinamide (a final concentration of 10 mM, Sigma-Aldrich, cat. no. N0636-100G), 1×B-27 supplement (Gibco, cat. no. 12587-010), Y27632 (a final concentration of 10 µM, Miltenyi Biotech, cat. no. 130-106-538), which are serum-free media, were used.

After counting the cell number of the cells separated in Experimental Example 17, the cells were centrifuged at 600×g for 5 minutes. Subsequently, the obtained cell pellet was suspended in the base medium, and suspended so that a cell density became 5×10$^4$ cells/mL.

Subsequently, 200 µL of the cell suspension was seeded per insert, and 400 µL of a base medium was added to the well below the insert and 3D cultured. The medium was replaced with a base medium every two to three days.

Experimental Example 19

(Passage of CD31$^-$CD45$^-$EpCAM$^+$ Bile Duct Epithelial Cell and Gallbladder Epithelial Cell)

The medium of the insert that reached confluence was removed, 300 µL of DMEM/Ham's F-12 with L-glutamine (Wako, cat. no. 048-29785) was added thereto. The mixture was stirred with a 1000 µL pipette and pipetted to break up the gel, and a colony was recovered in a 1.5 mL tube.

Subsequently, the tube was centrifuged at 600×g for 5 minutes, the supernatant was removed, and 1 ml of TripLETM (Gibco, cat. no. 12604021) was added thereto. Pipetting was performed 50 to 60 times with a 1000 µL pipette, and the tube was allowed to stand in a 37° C. constant-temperature tank for 5 minutes.

Subsequently, pipetting was performed again 50 to 60 times with a 1000 µL pipette, and the cells were allowed to pass through a 40 µm cell strainer (Falcon, cat. no. 352340). Subsequently, the tube was centrifuged at 600×g for 5 minutes, the supernatant was removed, and 1000 µL of DMEM/Ham's F-12 with L-glutamine (Wako, cat. no. 048-29785) was added thereto.

Subsequently, the tube was centrifuged at 600×g for 5 minutes, the supernatant was removed, and 100 µL of Matrigel was added per 2×10⁴ cell pellets to suspend the cell pellets. The cell suspension was seeded on the insert and allowed to stand at 37° C. for 30 minutes for gelation. Subsequently, 500 µL of a base medium was also added to the well under the insert and 3D cultured. The medium was replaced with a base medium every two to three days.

Experimental Example 20

(Introduction of Oncogene into Bile Duct Epithelial Cell and Gallbladder Epithelial Cell)

50 µL of Matrigel was put in a 0.4 µm cell culture insert in advance, and allowed to stand at 37° C. for 30 minutes for gelation.

Subsequently, the third to fourth passages of $CD31^-CD45^-EpCAM^l$ bile duct epithelial cells and $CD31^-CD45^-EpCAM^+$ gallbladder epithelial cells were respectively cell-pelleted with the same means as in the passage.

Subsequently, the thawed virus solution produced in Experimental Example 7 was added, and the cell pellets were suspended so that a cell density became 2×10⁴ cells/200 µL. Subsequently, 200 µL of the cell suspension was seeded per insert, and 400 µL of a base medium was added to the well below the insert and cultured in three dimensions. The medium was changed to a base medium after 3 days, and passaged 7 days later.

14 days after virus infection, a cell pellet was obtained with the same means as in the passage. Subsequently, the cell pellet was suspended in a washing buffer supplemented with PI (a final concentration of 0.1 µg/mL), DNase I (a final concentration of 0.1 mg/mL, Sigma-Aldrich, cat. no. DN25-100MG), Y27632 (a final concentration of 10 µM, Miltenyi Biotech, cat. no. 130-106-538), Penicillin (a final concentration of 100 U/mL, Nacalai Tesque, cat. no. 26253-84), Streptomycin (a final concentration of 100 µg/mL, Nacalai Tesque, cat. no. 26253-84), and Amphotericin B (a final concentration of 0.25 µg/mL, Gibco, cat. no. 15240-062). GFP-positive cells were separated with a flow cytometer (type "MoFlo XDP flow cytometer," Beckman Coulter, Inc.).

The separated cells were suspended in Matrigel and seeded on inserts. 500 µL of a base medium was added to the well under the insert and 3D cultured, and the medium was changed every 2 to 3 days. The cell colonies became confluent in about one week. Cells that reached confluence were passaged in the same manner as in Experimental Example 19.

Experimental example 21

(Transplantation (Into Liver) of Bile Duct Epithelial Cell and Gallbladder Epithelial Cell into which Oncogene has been Untroduced)

The bile duct epithelial cells and gallbladder epithelial cells into which the oncogene, $KRAS^{G12V}$ was introduced and which was produced in Experimental Example 20 were respectively transplanted into the liver of a wild-type C57BL6/J mouse. Specifically, first, the medium of the insert in which cells reached confluence was removed, 300 µL of DMEM/Ham's F-12 with L-glutamine (Wako, cat. no. 048-29785) was added thereto. The mixture was stirred with a 1000 µL pipette and pipetted to break up the gel, and a colony was recovered in a 1.5 mL tube.

Subsequently, the 1.5 mL tube was centrifuged at 600×g for 5 minutes, the supernatant was removed, and 1 mL of TripLETM (Gibco, cat. no. 12604021) was added thereto. Pipetting was performed 50 to 60 times with a 1000 µL pipette, and the tube was allowed to stand in a 37° C. constant-temperature tank for 5 minutes.

Subsequently, pipetting was performed again 50 to 60 times with a 1000 µL pipette, and the cells were allowed to pass through a 40 µm cell strainer (Falcon, cat. no. 352340). Subsequently, the tube was centrifuged at 600×g for 5 minutes, the supernatant was removed, and 1000 µL of DMEM/Ham's F-12 with L-glutamine (Wako, cat. no. 048-29785) was added thereto. Subsequently, the tube was centrifuged at 600×g for 5 minutes, the supernatant was removed, and 50 µL of Matrigel was added per 5×10⁴ cell pellets to suspend the cell pellets, and the cell pellets were allowed to stand at 4° C.

Subsequently, per mouse body weight (g), 10 µL of an anesthesia solution containing medetomidine 0.03 mg/mL, midazolam 0.4 mg/mL, and butorphanol 0.5 mg/mL was intraperitoneally injected to the wild-type C57BL6/J mouse to anesthetize it.

Subsequently, about 1 cm of the ventral midline skin was incised, the peritoneal membrane just above the liver was incised, and the left lobe of the liver was pulled out of the abdominal cavity. Subsequently, a syringe attached with a 29G injection needle was inserted, and 50 µL of the prepared Matrigel and the suspended cells were injected. After the injection, hemostasis was performed. Subsequently, the liver was returned to the abdominal cavity. The peritoneal membrane was sutured by one stitch, and the skin was sutured by two stitches to close the wound.

Figure 14:
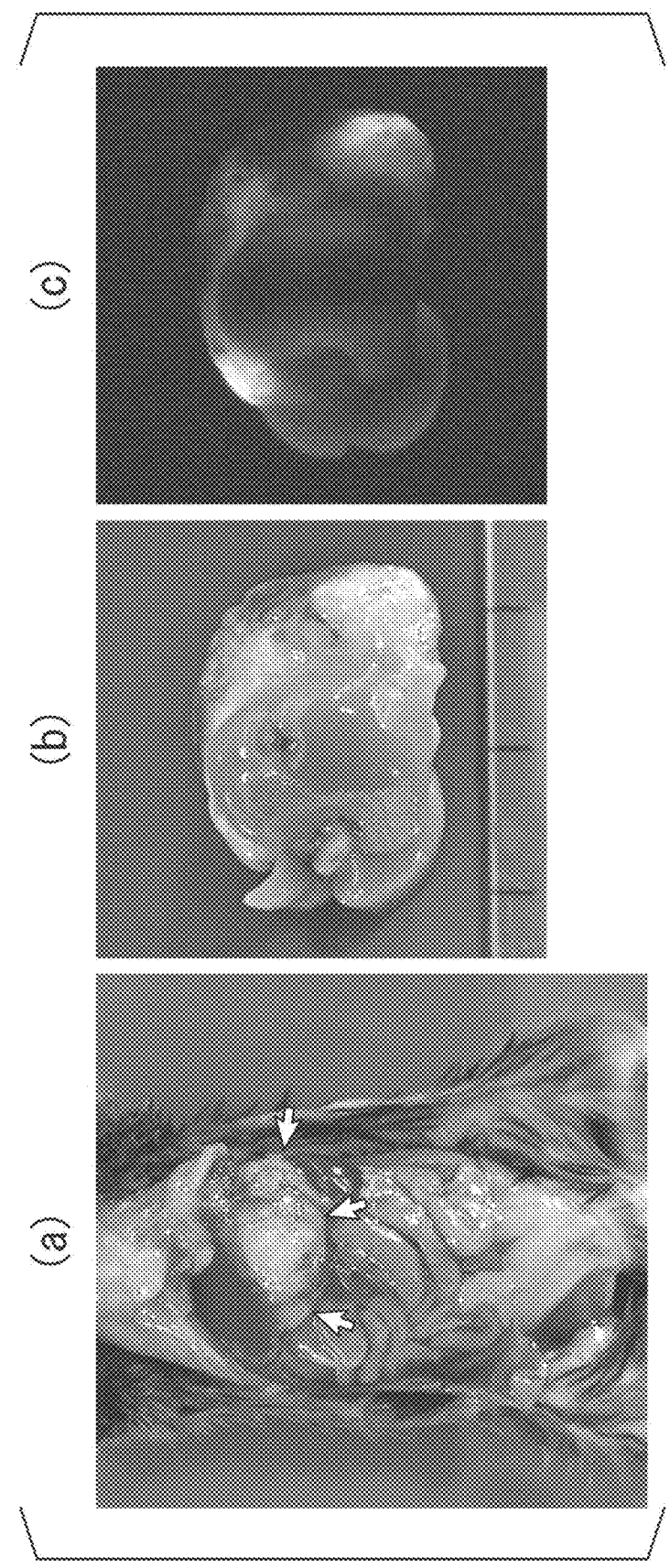
FIG. 14(a) is a photograph of the liver of a mouse into which bile duct epithelial cells into which an oncogene had been introduced had been transplanted in Experimental Example 21.
FIG. 14(b) is a photograph of the liver excised from the mouse shown in FIG. 14(a).
FIG. 14(c) is a photograph showing a result of detecting fluorescence of GFP in the liver shown in FIG. 14(b).

After breeding for 28 days from the cell transplantation, each mouse was euthanized, and the liver was exposed for observation. FIG. 14(a) is a photograph of the liver of a mouse into which bile duct epithelial cells into which an oncogene had been introduced had been transplanted. As a result, it was confirmed that a tumor was formed in the liver. Arrows in FIG. 14(a) indicate sites where tumors were formed.

FIG. 14(b) is a photograph of the liver excised from the mouse shown in FIG. 14(a). In addition, FIG. 14(c) is a photograph showing a result of detecting fluorescence of GFP in the liver shown in FIG. 14(b).

Figure 15:
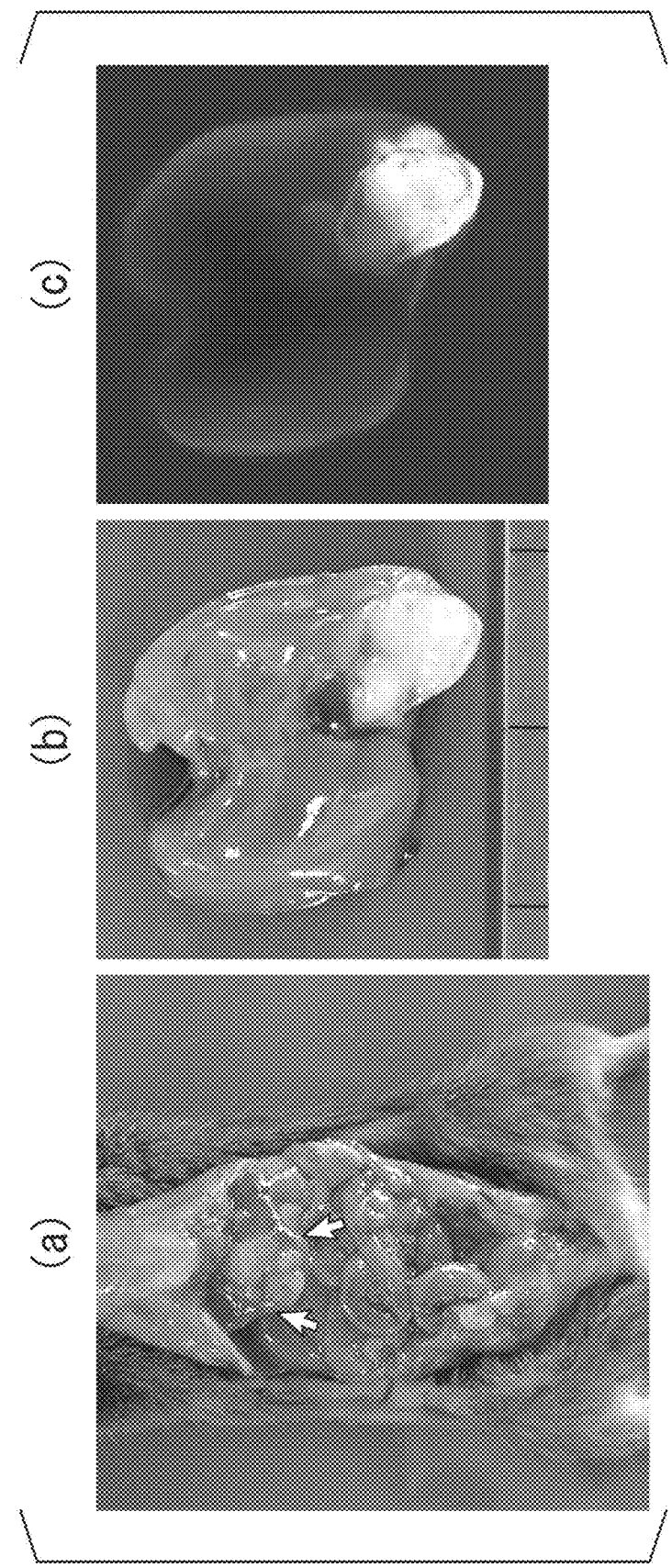
FIG. 15(a) is a photograph of the liver of a mouse into which gallbladder epithelial cells into which an oncogene had been introduced had been transplanted in Experimental Example 21.
FIG. 15(b) is a photograph of the liver excised from the mouse shown in FIG. 15(a).
FIG. 15(c) is a photograph showing a result of detecting fluorescence of GFP in the liver shown in FIG. 15(b).

FIG. 15(a) is a photograph of the liver of a mouse into which gallbladder epithelial cells into which an oncogene had been introduced had been transplanted. As a result, it was confirmed that a tumor was formed in the liver. Arrows in FIG. 15(a) indicate sites where tumors were formed.

FIG. 15(b) is a photograph of the liver excised from the mouse shown in FIG. 15(a). In addition, FIG. 15(c) is a photograph showing a result of detecting fluorescence of GFP in the liver shown in FIG. 15(b).

Based on the above results, it has become clear that a cancer-bearing model can be produced by transplanting bile duct epithelial cells into which an oncogene has been introduced into a wild-type mouse.

In addition, it has become clear that a cancer-bearing model can also be produced by transplanting gallbladder epithelial cells into which an oncogene has been introduced into a wild-type mouse.

INDUSTRIAL APPLICABILITY

According to the present invention, it is possible to provide a technique for producing cancer cells having various gene mutations, and for easily producing a cancer-bearing animal model that has a normal immune system.

The invention claimed is:

1. A cell population of epithelial tissue stem cells derived from an adult,
   wherein the epithelial tissue stem cells are lung, gall bladder or bile duct epithelial cells and wherein the epithelial tissue stem cells lack at least one tumor suppressor gene and the cell population expresses Epithelial cell adhesion molecule (EpCAM) and Stem cell antigen-1 (Sca-1), and wherein 50% or more of the EpCAM$^+$ cells in the cell population are Sca-1$^+$.

2. The cell population according to claim 1, which is CD31$^-$CD45$^-$.

3. The cell according to claim 1, which expresses Surfactant protein-C(SPC) and Secretoglobin family 1A member 1 (CC10).

4. The cell population according to claim 1, which expresses Lymphocyte antigen 6 family member D (Ly6D).

5. The cell population according to claim 1, which expresses Cytokeratin 19 (CK19).

6. The cell population according to claim 1, wherein the tumor suppressor gene is selected from the group consisting of Ink4a/Arf, p53, and PTEN.

7. The cell population according to claim 1, which further expresses at least one oncogene.

8. The cell population according to claim 7, wherein the oncogene is a mutated KRAS gene, a mutated EGFR gene, an ALK fusion gene, or a ROS1 fusion gene.

* * * * *